(12) United States Patent
McCarthy

(10) Patent No.: US 9,351,808 B2
(45) Date of Patent: May 31, 2016

(54) APPARATUS FOR REMOVING DENTAL APPLIANCE AND DENTAL SYSTEM

(75) Inventor: Sharon M. E. McCarthy, Frankfort, IL (US)

(73) Assignees: Sharon M. E. McCarthy, Frankfort, IL (US); Robert E. McCarthy, Frankfort, IL (US)

( * ) Notice: Subject to any disclaimer, the term of this patent is extended or adjusted under 35 U.S.C. 154(b) by 3 days.

(21) Appl. No.: 13/246,453

(22) Filed: Sep. 27, 2011

(65) Prior Publication Data
US 2013/0078592 A1    Mar. 28, 2013

(51) Int. Cl.
*A61C 7/08*    (2006.01)
*A61C 7/02*    (2006.01)

(52) U.S. Cl.
CPC .. *A61C 7/023* (2013.01); *A61C 7/08* (2013.01)

(58) Field of Classification Search
CPC ................................. A61C 7/08; A61C 7/023
USPC ........ 433/141, 6; 15/236.01, 236.07; D32/46; 30/324
See application file for complete search history.

(56) References Cited

U.S. PATENT DOCUMENTS

| | | | |
|---|---|---|---|
| 598,306 A | 2/1898 | Henderson | |
| 659,182 A | 10/1900 | Pilling | |
| 1,472,462 A | 10/1923 | de Port | |
| 1,474,497 A | 11/1923 | Stolper | |
| 1,691,786 A | 11/1928 | Roth | |
| 1,746,877 A * | 2/1930 | Tompkins | 132/333 |
| 2,457,231 A | 12/1948 | Henderson | |
| 2,634,497 A * | 4/1953 | Waldesbuehl | 30/142 |
| 2,863,444 A | 12/1958 | Winsten | |
| 3,154,069 A | 10/1964 | Ring | |
| D210,549 S * | 3/1968 | O'Brien | D7/653 |
| 3,393,451 A | 7/1968 | Rasch | |
| 3,651,800 A | 3/1972 | Wilbanks | |
| 4,616,867 A * | 10/1986 | O'Hara | 294/180 |
| 4,772,202 A | 9/1988 | Ebner, Jr. | |

(Continued)

FOREIGN PATENT DOCUMENTS

EP    0 399 237 B1    4/1990
WO    WO 2013/049355 A1    4/2013

OTHER PUBLICATIONS

Dentsply International, "The Appliance Remover Tool," taken from the web at http://essix.com/orstore/ShowItem.aspx?productID=ART01, Mar. 24, 2011, 1 pg.

(Continued)

*Primary Examiner* — Ralph Lewis
(74) *Attorney, Agent, or Firm* — Leydig, Voit & Mayer, Ltd.

(57) ABSTRACT

An apparatus for removing a dental appliance can include a body having a perimeter and a pry lip extending from the perimeter of the body. The pry lip includes a terminal ridge surface and an inclined surface disposed between the terminal ridge surface and the perimeter of the body. The apparatus for removing a dental appliance can be incorporated in a dental system which includes a dental appliance and the apparatus for removing a dental appliance. The apparatus for removing a dental appliance can be configured such that it fits within an area defined by an outer edge of the dental appliance. Thus, the dental appliance and the apparatus for removing the dental appliance can be stored within a dental appliance container with an internal cavity that closely conforms to the shape and size of the dental appliance.

6 Claims, 19 Drawing Sheets

(56) References Cited

U.S. PATENT DOCUMENTS

| | | | |
|---|---|---|---|
| 4,904,183 A | 2/1990 | Hannan et al. | |
| 5,092,050 A * | 3/1992 | Bardeen | 30/324 |
| 5,397,330 A | 3/1995 | Mikhail | |
| D380,653 S * | 7/1997 | Ayon | D7/696 |
| 5,876,409 A | 3/1999 | Heitz | |
| 5,928,254 A * | 7/1999 | Jensen | 606/161 |
| 5,975,893 A | 11/1999 | Chishti et al. | |
| 6,145,204 A | 11/2000 | Cash | |
| 6,183,248 B1 | 2/2001 | Chishti et al. | |
| 6,360,442 B2 | 3/2002 | O'Brien et al. | |
| D457,638 S | 5/2002 | Alstad et al. | |
| 6,390,812 B1 | 5/2002 | Chishti et al. | |
| 6,485,298 B2 | 11/2002 | Chishti et al. | |
| 6,752,380 B1 | 6/2004 | Taylor et al. | |
| 6,776,616 B2 | 8/2004 | Dryer | |
| 7,011,517 B2 | 3/2006 | Nicozisis | |
| D545,518 S * | 6/2007 | Ayala et al. | D32/46 |
| 7,448,514 B2 | 11/2008 | Wen | |
| 7,482,053 B2 | 1/2009 | Swiontek | |
| D609,858 S * | 2/2010 | Ezell | D28/36 |
| 7,904,307 B2 | 3/2011 | Abolfathi et al. | |
| 8,152,525 B2 * | 4/2012 | Rossi, III | 433/167 |
| 8,167,612 B2 * | 5/2012 | DeSanti | 433/3 |
| 2005/0064358 A1 | 3/2005 | Nicozisis | |
| 2007/0072142 A1 | 3/2007 | Staines et al. | |
| 2008/0160473 A1 | 7/2008 | Li et al. | |
| 2009/0246732 A1 | 10/2009 | Creasman et al. | |
| 2009/0258323 A1 | 10/2009 | Saubers | |
| 2009/0286199 A1 | 11/2009 | Creasman et al. | |
| 2011/0045427 A1 | 2/2011 | DeSanti | |
| 2012/0197304 A1 | 8/2012 | Medoff et al. | |
| 2013/0330682 A1 | 12/2013 | McCarthy | |

OTHER PUBLICATIONS

Thefont, "How to Remove Invisalign Braces Easily—Even When You Have Attachments 80," taken from the web at http://hubpages.com/hub/How-To-Remove-Invasalign-Braces, Sep. 15, 2010, 5 pgs.

"Wearing and Using Your Invisalign Aligners," publicly available prior to Sep. 27, 2011, 2 pgs.

"The Outie Is a Tool to Remove Invisalign Braces Safely and Easily!," taken from the web at http://www.outietool.com, Sep. 24, 2009, 2 pgs.

International Search Report and Written Opinion in International Application No. PCT/US2012/057570; Dec. 4, 2012.

International Search Report and Written Opinion in International Application No. PCT/US2013/061622; Dec. 13, 2013.

* cited by examiner

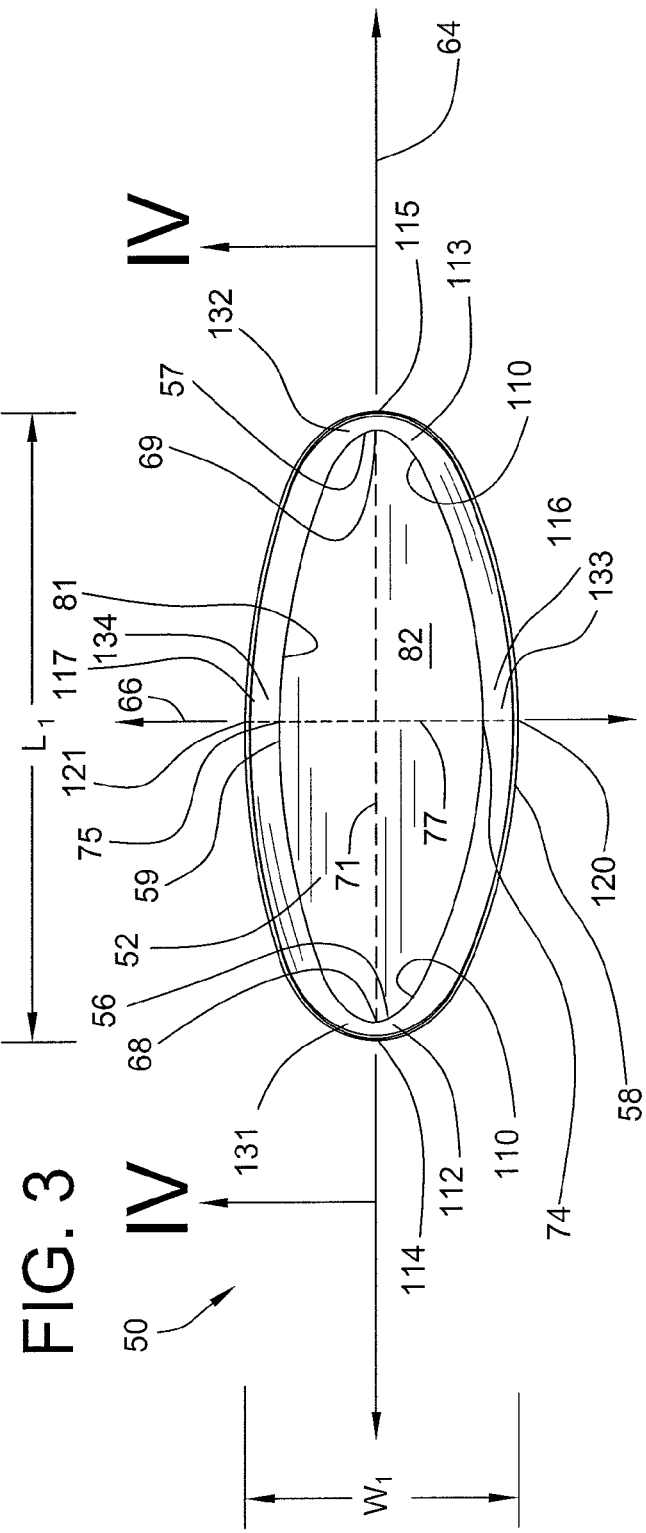

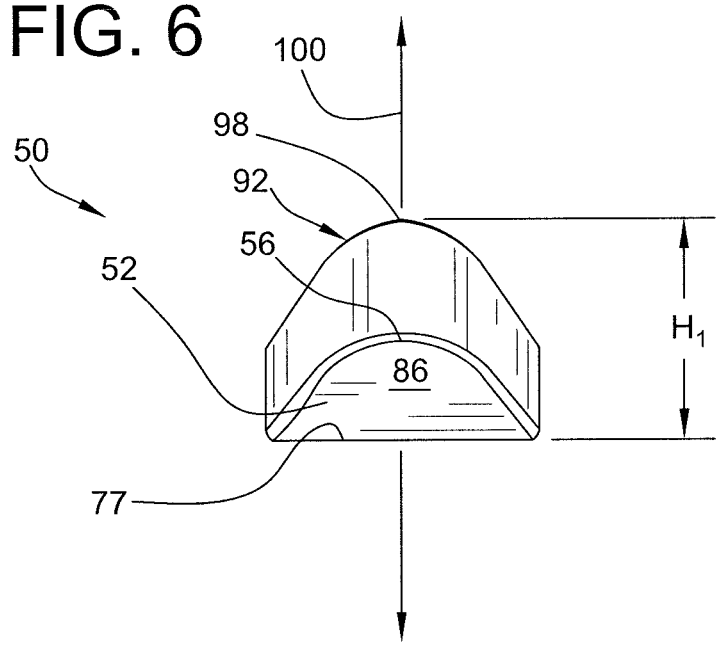
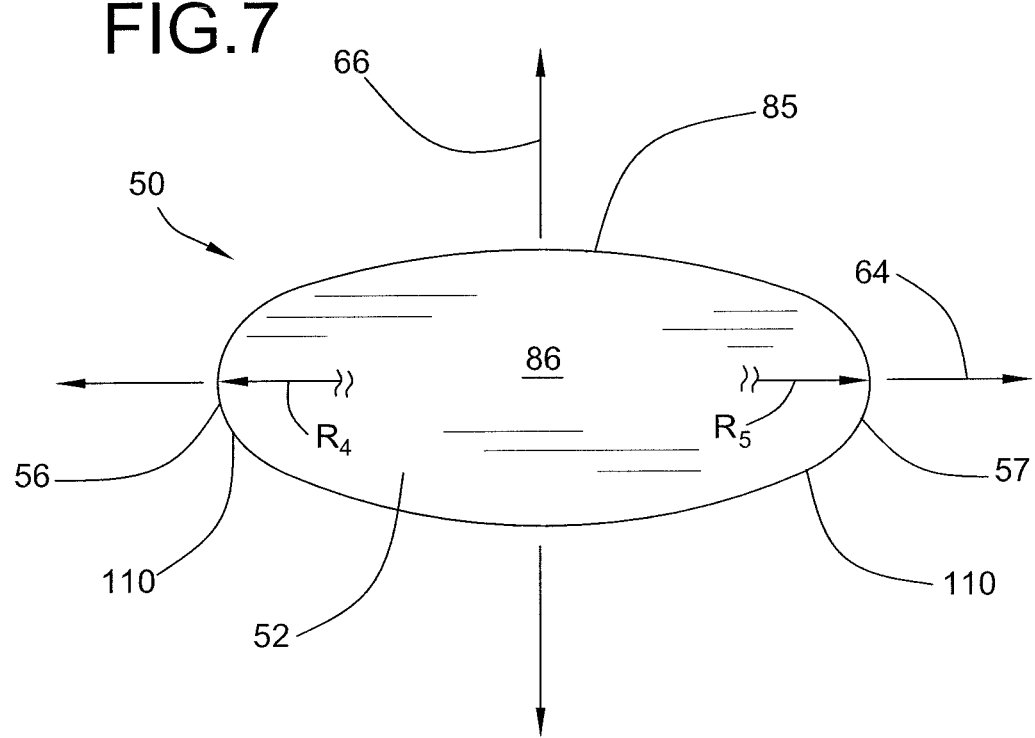

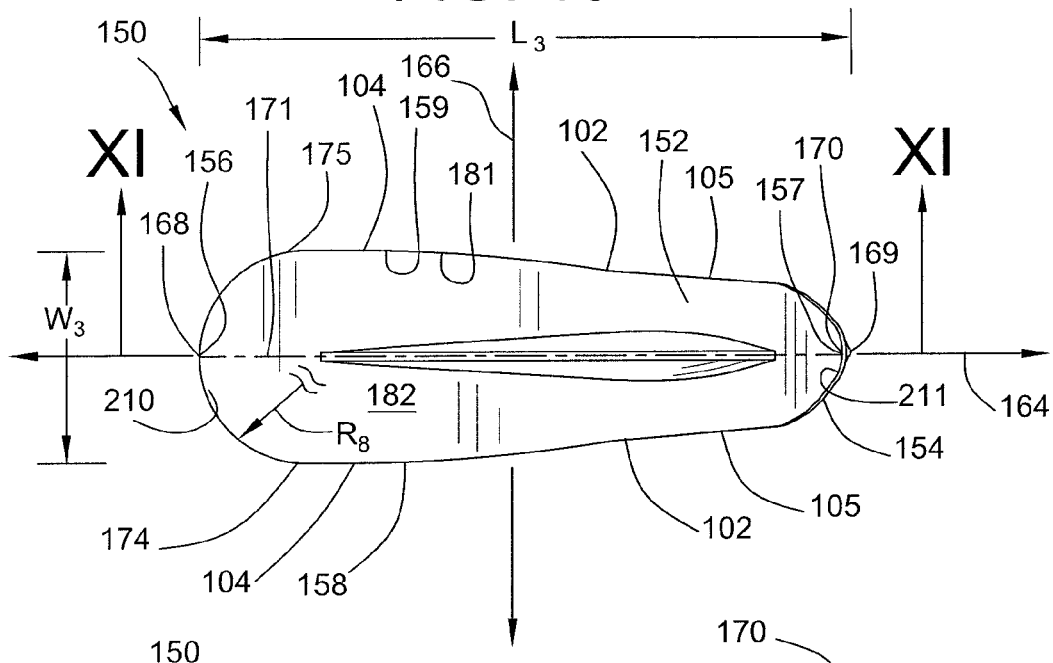
FIG. 10
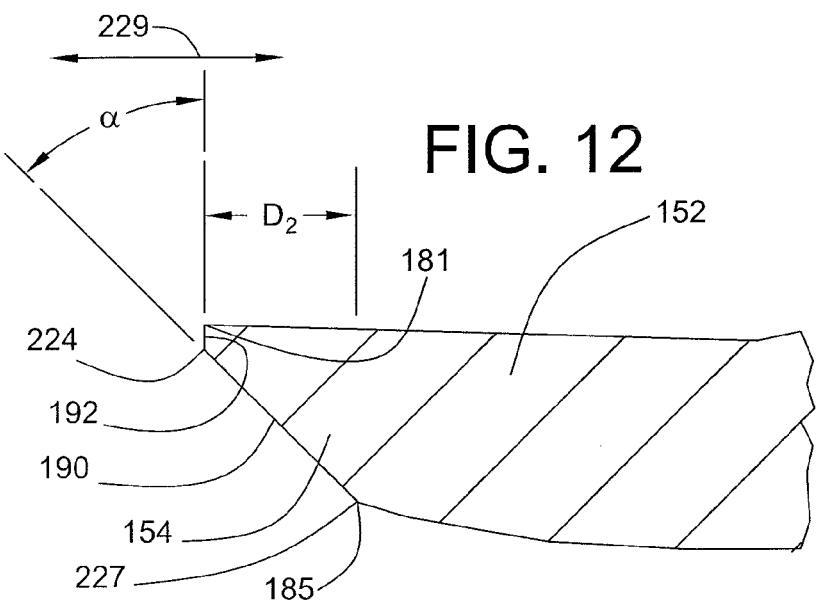
FIG. 11
FIG. 12

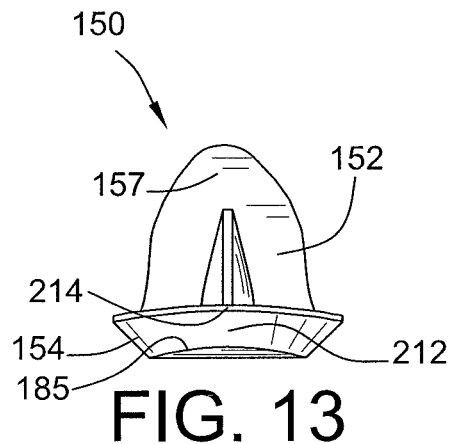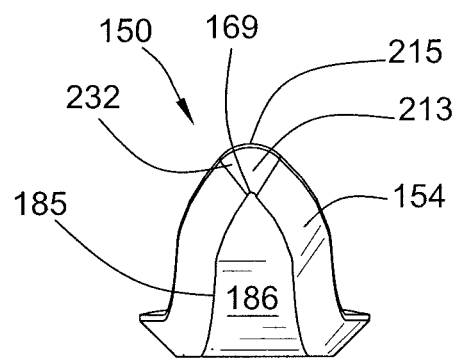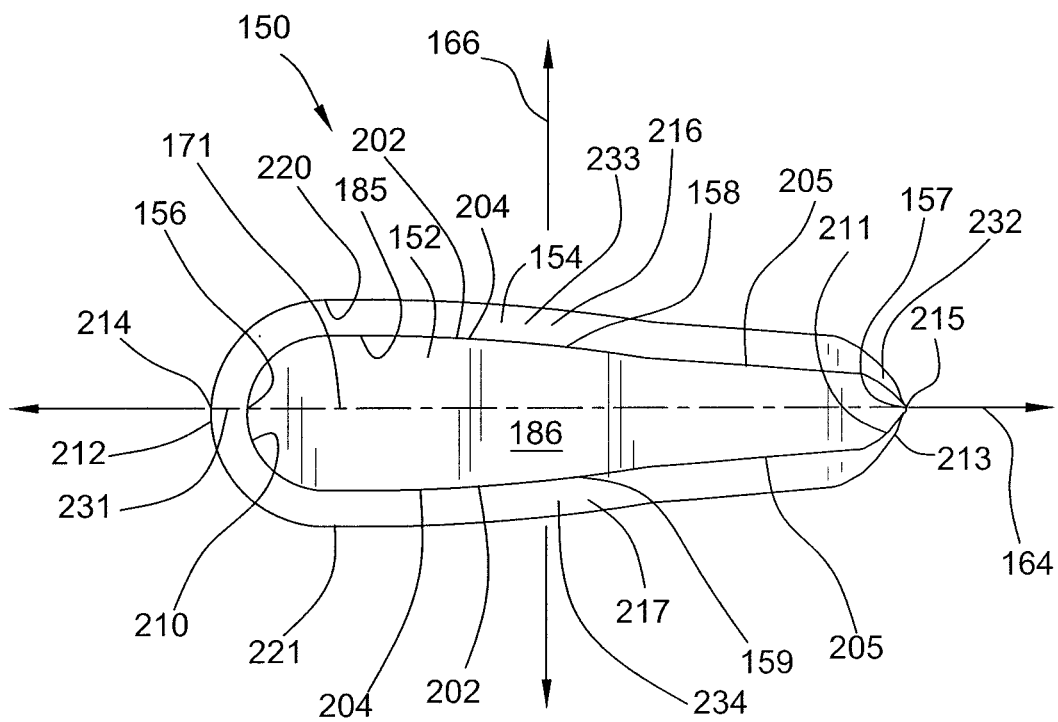

FIG. 18
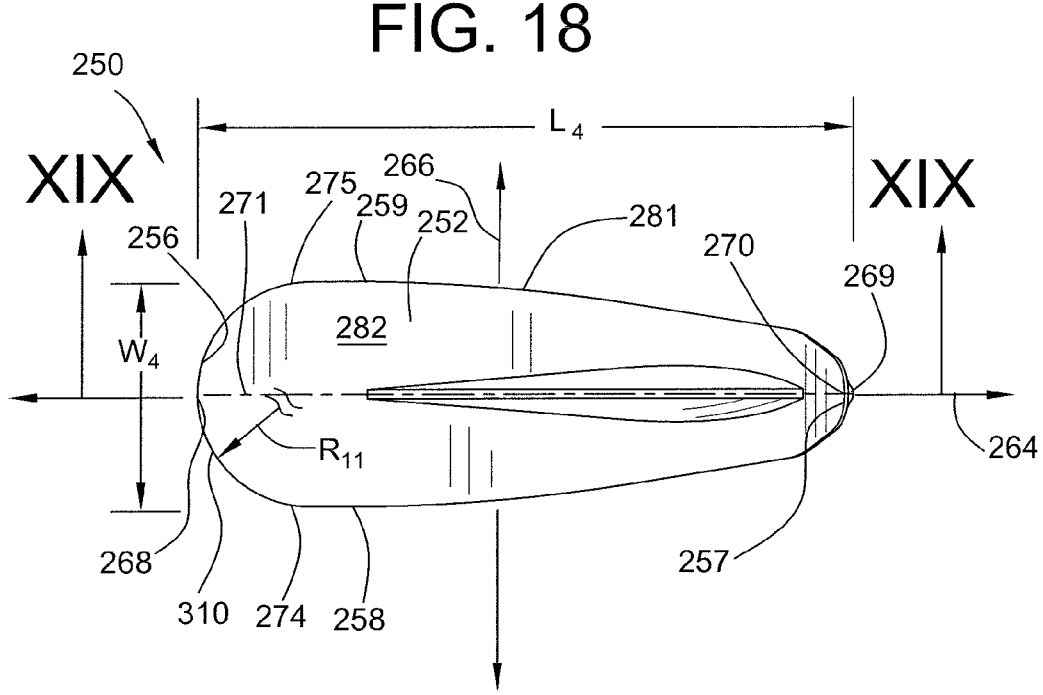
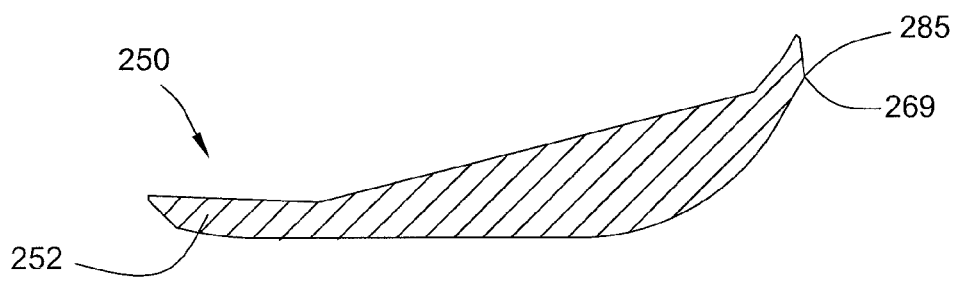
FIG. 19
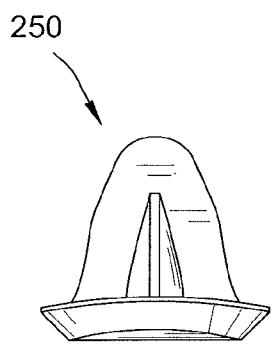
FIG. 20
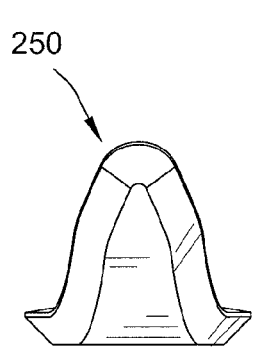
FIG. 21

APPARATUS FOR REMOVING DENTAL APPLIANCE AND DENTAL SYSTEM

TECHNICAL FIELD

This patent disclosure relates generally to dental appliances and, more particularly, to an apparatus for removing a dental appliance and a dental system including the same.

BACKGROUND

Removable dental appliances, such as clear plastic tooth-positioning appliances and retainers, have been used in orthodontic treatments as an alternative to braces and other bonded orthodontic equipment for controlled tooth movement to, and/or for retaining teeth in, a predetermined position. Such a dental appliance can be made so that it is removable to allow a wearer to periodically remove the dental appliance to eat, drink, brush, floss, etc.

U.S. Pat. Nos. 5,975,893 and 6,183,248 provide an example of such removable tooth-positioning appliances. A patient is typically provided a plurality of appliances which are configured to be placed successively on the patient's teeth to incrementally reposition the teeth from an initial tooth arrangement to a final tooth arrangement. The set of appliances given to a patient have geometries selected to progressively reposition the teeth from the initial tooth arrangement, through successive intermediate arrangements and, ultimately, to the final tooth arrangement.

To achieve the movement of a tooth from one position to another position, such a tooth-positioning appliance can be relatively rigid. The stiffness of the appliance provides the re-positioning force necessary to move the teeth and ensures that the dental appliance remains securely placed on the wearer's teeth.

An appliance wearer may remove the positioning appliance frequently throughout the day. The stiffness of the dental appliance and the typically tightly-conforming fit of the dental appliance to the wearer's teeth can make it difficult for the wearer to remove the appliance. Appliance wearers are typically instructed to use their fingers and fingernails to remove the appliances, but they often find removing the appliances to be difficult and in many cases painful.

U.S. Patent Application Publication No. US 2009/0258323 is entitled, "Outie Tool for Removal of a Plastic Tooth Positioning Appliance or Aligner (Invisible Braces) From Teeth of a Patient." The "Outie Tool" is a straight rigid barrel with a lever appendage on one proximal end for removing a lower aligner and a hook appendage on the other end for removing an upper aligner. Such prior removal tools can be difficult for many appliance wearers to use effectively. As such, there continues to be a need to provide a compact and convenient tool that is specifically designed to remove a dental appliance from a user's teeth in a safe and effective manner.

It will be appreciated that this background description has been created by the inventor to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

SUMMARY

Embodiments of an apparatus for removing a dental appliance and of a dental system are disclosed. In an embodiment, an apparatus for removing a dental appliance includes a body and a pry lip. The body includes a first perimeter defining a first face having a concave surface and a second perimeter defining a second face having a convex surface. The first face is in opposing relationship to the second face. The pry lip extends from one of the first and second perimeters. The pry lip includes an inclined surface and a terminal ridge surface. The inclined surface is disposed between the terminal ridge surface and the one of the first and second perimeters from which the pry lip extends.

In another embodiment, an apparatus for removing a dental appliance includes a body having a perimeter and a pry lip extending from the perimeter of the body. The pry lip includes an inclined surface and a terminal ridge surface. The inclined surface is disposed between the terminal ridge surface and the perimeter of the body.

In still another embodiment, an apparatus for removing a dental appliance includes a body and a pry lip. The body extends along a first axis and a second axis, which is perpendicular to the first axis. The body includes a pair of opposing ends in spaced relationship along the first axis and a pair of opposing sides in spaced relationship along the second axis. The pry lip extends from the body and is configured such that a first pry lip portion is disposed adjacent to one of the opposing ends and the opposing sides of the body and a second pry lip portion is disposed adjacent to another of the opposing ends and the opposing sides of the body.

In yet another embodiment, a dental system includes a dental appliance and an apparatus for removing a dental appliance. The dental appliance includes an outer edge defining a dental appliance area with a first shape. The apparatus for removing a dental appliance includes an outer edge defining a remover area with a second shape. The apparatus for removing a dental appliance is configured such that the second shape of the remover area is disposable within the first shape of the dental appliance area

BRIEF DESCRIPTION OF THE DRAWINGS

FIG. 3 is a top plan view of the apparatus for removing a dental appliance of FIG. 1.

FIG. 4 is a cross-sectional view taken along line IV-IV in FIG. 3.

FIG. 6 is an end elevational view of the apparatus for removing a dental appliance of FIG. 1. The opposing end elevational view of the apparatus for removing a dental appliance of FIG. 1 is identical to the view shown in FIG. 6.

FIG. 7 is a bottom plan view of the apparatus for removing a dental appliance of FIG. 1.

FIG. 10 is a top plan view of the apparatus for removing a dental appliance of FIG. 8.

FIG. 11 is a cross-sectional view taken along line XI-XI in FIG. 10.

FIG. 12 is an enlarged, detail view taken from FIG. 11.

FIG. 13 is a first end elevational view of the apparatus for removing a dental appliance of FIG. 8.

FIG. 14 is a second end elevational view of the apparatus for removing a dental appliance of FIG. 8.

FIG. 15 is a bottom plan view of the apparatus for removing a dental appliance of FIG. 8.

FIG. 18 is a top plan view of the apparatus for removing a dental appliance of FIG. 16.

FIG. 19 is cross-sectional view taken along line XIX-XIX in FIG. 18.

FIG. 20 is a first end elevational view of the apparatus for removing a dental appliance of FIG. 16.

FIG. 21 is a second end elevational view of the apparatus for removing a dental appliance of FIG. 16.

DETAILED DESCRIPTION

Figure 1:
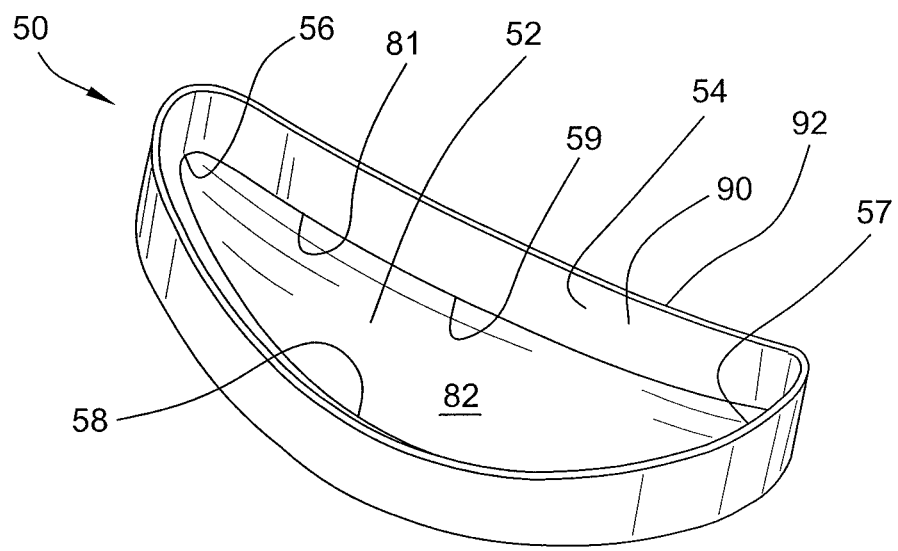
FIG. 1 is a perspective view of an embodiment of an apparatus for removing a dental appliance constructed according to principles of the present disclosure.

Embodiments of an apparatus for removing a dental appliance and of a dental system are disclosed herein. In an embodiment, an apparatus for removing a dental appliance includes a body having a perimeter and a pry lip extending from the perimeter of the body. The pry lip includes an inclined surface and a terminal ridge surface. The inclined surface is disposed between the terminal ridge surface and the perimeter of the body. The inclined surface can be inclined with respect to at least the terminal ridge surface. In some embodiments, the inclined surface can be inclined with respect to the terminal ridge surface and the portion of the body that is adjacent to the inclined surface.

The pry lip can be configured such that the terminal ridge surface can be inserted between an appliance wearer's teeth and the dental appliance to facilitate removal of the dental appliance from the wearer's teeth. The inclined surface can be configured to aid the wearer in the removal process by acting as a lever to pry the dental appliance away from the wearer's teeth. The pry lip can be configured such that a proximal base of the pry lip adjacent the perimeter of the body acts as a stop to prevent the dental appliance wearer from inserting the pry lip between the wearer's teeth and the dental appliance beyond a predetermined distance. By limiting the distance that the pry lip can be inserted between the wearer's teeth and the dental appliance, the wearer can avoid injuring the wearer's gums with the apparatus for removing a dental appliance.

In another embodiment, an apparatus for removing a dental appliance includes a body and a pry lip. The body includes a first perimeter defining a first face having a concave surface and a second perimeter defining a second face having a convex surface. The first face is in opposing relationship to the second face. The pry lip extends from one of the first and second perimeters. The pry lip includes an inclined surface and a terminal ridge surface. The inclined surface is disposed between the terminal ridge surface and the one of the first and second perimeters from which the pry lip extends.

The concave surface and convex surface can each have a radius of curvature that is configured to help position the pry lip within the wearer's mouth between the teeth and the dental appliance in a plurality of orientations and can help create a wrapping action with the teeth when prying the dental appliance from the wearer's teeth. In some embodiments, the concave surface can have a different radius of curvature than the convex surface.

In still another embodiment, an apparatus for removing a dental appliance includes a body and a pry lip. The body extends along a first axis and a second axis, which is perpendicular to the first axis. The body includes a pair of opposing ends in spaced relationship along the first axis and a pair of opposing sides in spaced relationship along the second axis. The pry lip extends from the body and is configured such that a first pry lip portion is disposed adjacent to one of the opposing ends or the opposing sides of the body and a second pry lip portion is disposed adjacent to another of the opposing ends and/or the opposing sides of the body.

In some embodiments, the pry lip can be configured such that the user can grip the apparatus in a plurality of different positions. By changing the gripping position, the dental appliance wearer can take advantage of the different orientations provided by the pry lip and, in some embodiments, the curved portions of the body, to facilitate the positioning of the pry lip between the dental appliance and the wearer's teeth to pry the dental appliance from the teeth. In some embodiments, the pry lip circumscribes the perimeter of the body. In some embodiments, the shape and size of the terminal ridge surface and the inclined surface of the pry lip remain substantially the same around the entire perimeter of the body.

In an embodiment, a dental system includes a dental appliance and an apparatus for removing a dental appliance. The dental appliance includes an outer edge defining a dental appliance area with a first shape. The apparatus for removing a dental appliance includes an outer edge defining a remover area with a second shape. The apparatus for removing a dental appliance is configured such that the dental appliance area is greater than or equal to the remover area and the second shape of the remover area is disposable within the first shape of the dental appliance area. The compact design of the apparatus for removing a dental appliance allows the apparatus to be stored with the dental appliance in a dental appliance container having an internal cavity that closely conforms to the shape and size of the dental appliance.

Turning now to the Figures, there is shown in FIGS. 1-7 an embodiment of an apparatus 50 for removing a dental appliance constructed in accordance with principles of the present disclosure. In the embodiment of FIGS. 1-7, the dental appliance removal device 50 is generally bowl-shaped. The removal device 50 is constructed such that it can be gripped by a user in a plurality of positions to vary the orientation of the removal device 50 relative to a dental appliance fitted to a user's teeth.

Figure 2:
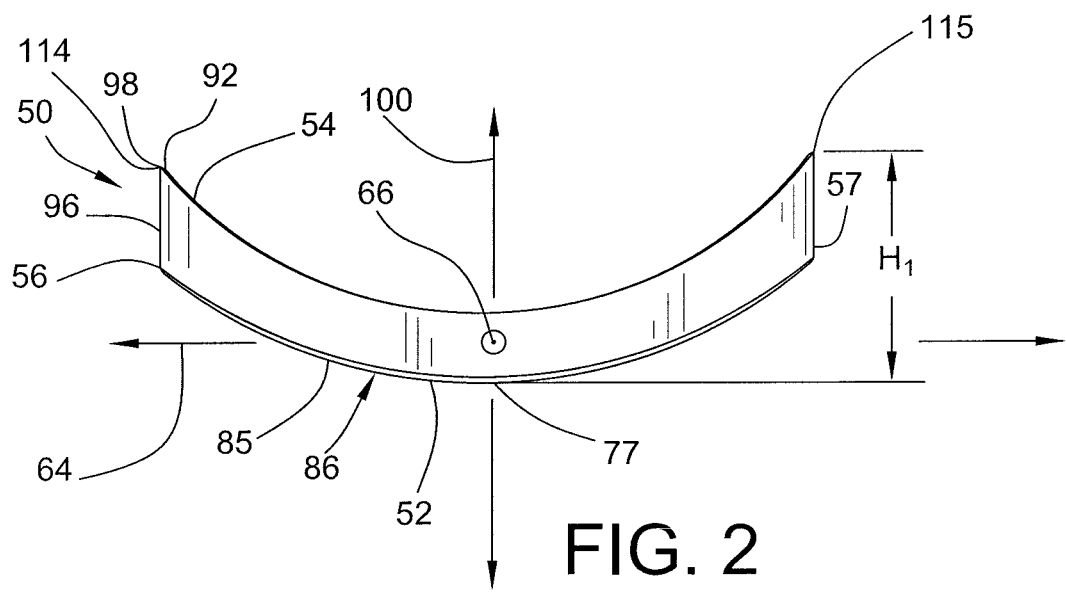
FIG. 2 is a side elevational view of the apparatus for removing a dental appliance of FIG. 1. The opposing side elevational view of the apparatus for removing a dental appliance of FIG. 1 is identical to the view shown in FIG. 2.

Referring to FIGS. 1 and 2, the apparatus 50 for removing a dental appliance includes a body 52 and a pry lip 54. The pry lip 54 circumscribes the body 52 and is adapted to facilitate the removal of a dental appliance from a wearer's teeth. The body 52 is configured to help allow a user to position a portion of the pry lip 54 in a plurality of orientations relative to a dental appliance mounted to the user's teeth.

The body 52 is generally elongate. The body 52 includes a pair of ends 56, 57 and a pair of sides 58, 59 in spaced relationship with each other. The sides 58, 59 extend between the ends 56, 57. The ends 56, 57 and the sides 58, 59 are each mirror images of the other respective end and side. The body 52 is generally arcuate from the first end 56 to the second end 57.

The body 52 can include at least one perimeter that defines a face having a curved surface. The curved surface can be concave or convex. In the illustrated embodiment, the body 52 includes a first perimeter 81 defining a first face 82 having a concave surface and a second perimeter 85 defining a second face 86 having a convex surface. Referring to FIGS. 3 and 7, the first perimeter 81 and the second perimeter 85 are both generally oval-shaped. The first face 82 is in opposing relationship to the second face 86.

Referring to FIGS. 1 and 2, the pry lip 54 can extend from one of the first and second perimeters 81, 85. In the illustrated embodiment of FIG. 1, the pry lip 54 extends from the first perimeter 81. The pry lip 54 includes an inclined surface 90 and a terminal ridge surface 92. The inclined surface 90 can be disposed between the terminal ridge surface 92 and the perimeter from which the pry lip 54 extends, in this case the first perimeter 81. The pry lip 54 can circumscribe the perimeter from which the pry lip 54 extends. The illustrated pry lip 54 of FIG. 1 circumscribes the first perimeter 81.

Referring to FIG. 3, the body 52 extends between the ends 56, 57 along a central longitudinal axis 64. The sides 58, 59 of the body 52 are in spaced relationship with each other along a transverse axis 66 that is perpendicular to the longitudinal axis. Each end 56, 57 includes an end apex 68, 69 that is located substantially at a lateral midline 71 between the sides 58, 59 along the transverse axis 66. Each side 58, 59 includes a side apex 74, 75 that is located substantially at a longitudinal midline 77 between the ends 56, 57 along the longitudinal axis 64.

Referring to FIG. 2, the pry lip 54 includes a sidewall 96 that extends between an outer perimeter 98 of the terminal ridge surface 92 and the second perimeter 85 of the body 52. The sidewall 96 circumscribes the second perimeter 85 and the terminal ridge surface 92. The sidewall 96 generally conforms to the curved shape of the body 52. The sidewall 96 is substantially parallel to a medial axis 100, which is perpendicular to the longitudinal axis 64 and the transverse axis 66.

Referring to FIG. 3, the pry lip 54 can be configured such that a user can grip the apparatus 50 at one of a plurality of different gripping locations and leave exposed at least one portion of the pry lip 54 for insertion between a dental appliance and the user's teeth to which the dental appliance is mounted. In conjunction with the curved shape of the body 52, the user can select one of a plurality of gripping positions to further facilitate the insertion of the pry lip 54 by providing a multitude of relative orientations between the pry lip 54 and the dental appliance mounted to the user's teeth.

Each end 56, 57 of the body 52 includes a curved portion 110 of the perimeters 81, 85. The pry lip 54 includes a rounded tip portion 112, 113 extending around the curved portions 110 of the perimeters 81, 85 of the body 52. Each rounded tip portion 112, 113 of the pry lip 54 includes a pry lip end apex 114, 115 that is located substantially at the lateral midline 71 along the transverse axis 66. The pry lip 54 also includes a pair of sides 116, 117 having a pry lip side apex 120, 121 that is located substantially at the longitudinal midline 77 along the longitudinal axis 64.

In some embodiments, the pry lip 54 can be configured such that a first pry lip portion is disposed adjacent to one of either the opposing ends 56, 57 or the opposing sides 58, 59 of the body 52 and a second pry lip portion is disposed adjacent to another one of the opposing ends 56, 57 and/or the opposing sides 58, 59 of the body 52. Accordingly, in some embodiments, the pry lip 54 can be configured such that a first pry lip portion is disposed adjacent to one of the opposing ends 56, 57 and a second pry lip portion is disposed adjacent to one of the opposing sides 58, 59 of the body 52. In yet other embodiments, the pry lip 54 can be configured such that the first and second pry lip portions are respectively disposed adjacent to the opposing ends 56, 57 of the body 52. In still other embodiments, the pry lip 54 can be configured such that the first and second pry lip portions are respectively disposed adjacent to the opposing sides 58, 59 of the body 52.

The illustrated pry lip 54 is configured such that it includes a pry lip portion 131, 132, 133, 134 respectively disposed adjacent to each of the opposing ends 56, 57 and the opposing sides 58, 59 of the body 52. The illustrated pry lip 54 extends continuously around the first perimeter 81 between the pry lip portions 131, 132, 133, 134 such that the portions 131, 132, 133, 134 of the pry lip 54 are contiguous. In other embodiments, the pry lip portions 131, 132, 133, 134 can be discontinuous. In still other embodiments, the pry lip 54 can include two or more pry lip portions disposed at different locations along the first perimeter 81.

Referring to FIG. 2, the ends 56, 57 are offset from the second face 86 of the body 52 at the longitudinal midline 77 along the medial axis 100 (see FIG. 6 also). The apparatus 50 has a height $H_1$, measured along the medial axis 100 between the bottom face 86 of the body 52 at the longitudinal midline 77 and the outer perimeter 98 of the terminal ridge surface 92 at one of the pry lip end apexes 114, 115. In the illustrated embodiment, the height $H_1$ is about 0.6 inches. In other embodiments, the height of the apparatus for removing a dental appliance can be different. For example, in other embodiments, the height $H_2$ can be about 0.5 inches.

Referring to FIG. 3, the apparatus 50 has a length $L_1$, measured along the central longitudinal axis 64 between the pry lip end apex 114, 115 of each rounded tip portion 112, 113 of the pry lip, that is greater than the width $W_1$, measured along the transverse axis 66 between the pry lip side apex 120, 121 of the pry lip sides 116, 117 at the longitudinal midline 77. In the illustrated embodiment the length $L_1$ is about 1.7 inches and the width $W_1$ is about 0.7 inches. In other embodiments, the length $L_1$ and the width $W_1$ can be different. For example, in some embodiments the length $L_2$ can be about 1.25 inches and the width $W_2$ can be about 0.6 inches. In some embodiments, the apparatus can have a length-to-width ratio of about 2 or more. The illustrated embodiment of FIG. 1 has a length-to-width ratio of about 2.4. In yet other embodiments, the apparatus can have a length-to-width ratio of between about 2 and about 3.

In the illustrated embodiment, the length $L_1$ is greater than the height $H_1$. The illustrated embodiment of FIG. 1 has a length-to-height ratio of about 2.8. In other embodiments, the apparatus can have a different length, a different height, and/or a different length-to-height ratio. For example, in some embodiments, the apparatus can have a length-to-height ratio of about 2 or more. In yet other embodiments, the apparatus can have a length-to-height ratio of about 2.6. In still other embodiments, the apparatus can have a length-to-height ratio of between about 2 and about 3.

In still other embodiments, the apparatus can be scaled either upwardly or downwardly to be more convenient for a user to manipulate with either relatively large fingers and/or teeth or relatively small fingers and/or teeth. For example, in some embodiments the apparatus can have a length $L_2$ of about 1.3 inches, a width $W_2$ of about 0.6 inches, and a height $H_2$ of about 0.5 inches.

Referring to FIG. 4, the concave surface of the first face 82 of the body 52 has a portion with a radius $R_1$ of concave body curvature along the central longitudinal axis 64. The concave surface of the first face 82 of the body 52 is generally a cylindrical segment bounded by the first perimeter 81 (see FIG. 3 also) and defined by a cylindrical axis that is substantially parallel to the transverse axis 66 disposed a first radial distance $R_1$, measured along the medial axis 100, from the concave surface. The convex surface of the second face 86 of the body 52 has a portion with a radius $R_2$ of convex body curvature along the central longitudinal axis 64. The convex surface of the second face 86 of the body 52 is generally a cylindrical segment bounded by the second perimeter 85 (see FIG. 7 also) and defined by a cylindrical axis that is substantially parallel to the transverse axis 66 disposed a second radial distance $R_2$, measured along the medial axis 100, from the convex surface. The radius $R_2$ of convex body curvature can be greater than the radius $R_1$ of concave body curvature.

The terminal ridge surface 92 of the pry lip 54 has a portion with a radius $R_3$ of concave pry lip curvature along the central longitudinal axis 64. The terminal ridge surface 92 of the pry lip 54 generally follows the curvature of the concave surface of the first face 82 of the body 52 and the outer perimeter 98 of the terminal ridge surface 92 can be defined a cylindrical axis that is substantially parallel to the transverse axis 66 disposed a third radial distance $R_3$, measured along the medial axis 100, from the outer perimeter 98 of the terminal ridge surface 92. The radius $R_2$ of convex body curvature and the radius $R_1$ of concave body curvature can be both greater than the radius $R_3$ of concave pry lip curvature. Other embodiments can have different relationships between these radii $R_1$, $R_2$, $R_3$ of curvature. For example, in some embodiments, the radius $R_3$ of concave pry lip curvature can be greater than the radius $R_1$ of concave body curvature.

The illustrated apparatus 50 of FIG. 4 has a radius $R_1$ of concave body curvature of about 1.1 inches, a radius $R_2$ of convex body curvature of about 1⅜ inches, and a radius $R_3$ of concave pry lip curvature of about 0.9 inches. The ratio of the radius $R_2$ of convex body curvature to the radius $R_1$ of concave body curvature is about 1.2. The ratio of the radius $R_2$ of convex body curvature to the radius $R_3$ of concave pry lip curvature is about 1.5. The ratio of the radius $R_1$ of concave body curvature to the radius $R_3$ of concave pry lip curvature is about 1.2.

In other embodiments, the radius $R_1$ of concave body curvature can be in a range from about a half inch to about 1½ inches. The radius $R_2$ of convex body curvature can be in a range from about ¾ inches to about 1¾ inches. The radius $R_3$ of concave pry lip curvature can be in a range from about a half inch to about 1¼ inches.

The ratio of the radius $R_2$ of convex body curvature to the radius $R_1$ of concave body curvature can be in a range from greater than one to about 2, and in other embodiments, in a range from greater than one to about 1.7. The ratio of the radius $R_2$ of convex body curvature to the radius $R_3$ of concave pry lip curvature can be in a range from greater than one to about 2, and in other embodiments, in a range from greater than one to about 1.5. The ratio of the radius $R_1$ of concave body curvature to the radius $R_3$ of concave pry lip curvature can be in a range from about 0.5 to about 2, and in other embodiments, in a range from greater than one to about 1.7.

Figure 5:
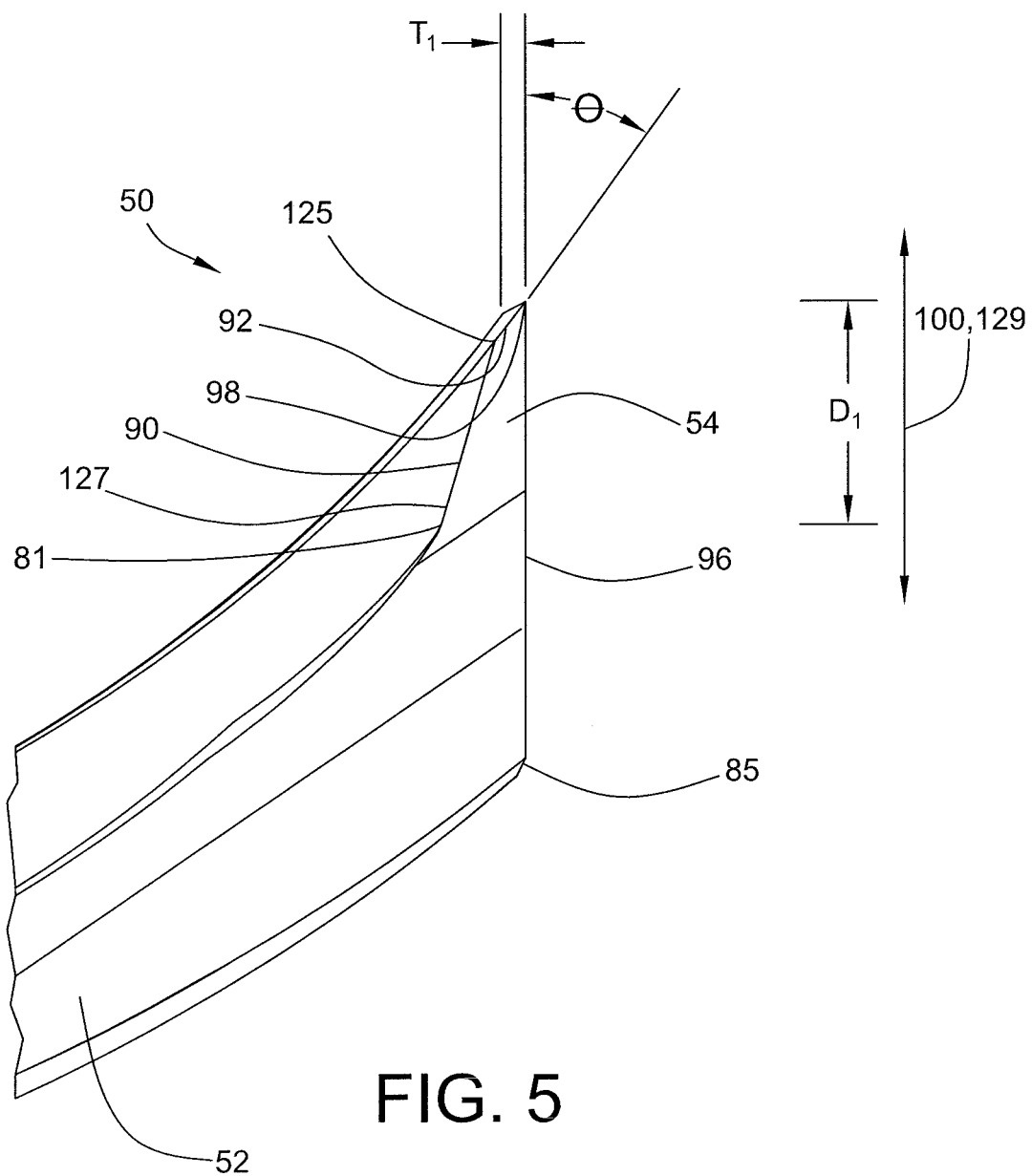
FIG. 5 is an enlarged, detail view taken from FIG. 4.

Referring to FIG. 5, the inclined surface 90 of the pry lip 54 is disposed adjacent the first perimeter 81 of the body 52. The terminal ridge surface 92 defines an oblique bevel angle $\theta$ with respect to the sidewall 96. In some embodiments, the bevel angle $\theta$ can be in a range between about 20° and about 75°. The illustrated bevel angle $\theta$ is about 45°.

The terminal ridge surface 92 is adapted to be inserted between a dental appliance and the teeth to which the appliance is mounted. The terminal ridge surface 92 of the pry lip 54 can have a thickness $T_1$, measured along the longitudinal axis 64 between the outer perimeter 98 and an inner perimeter 125, that is configured to facilitate the insertion of the pry lip 54 between a user's teeth and a dental appliance mounted thereto. In a preferred embodiment, the thickness $T_1$ of the terminal ridge surface 92 is about 0.025 inches or less, and even more preferably about 0.02 inches or less. The thickness $T_1$ of the illustrated terminal ridge surface 92 is about 0.015 inches. The bevel angle $\theta$ between the terminal ridge surface 92 and the sidewall 96 can be adapted to facilitate the insertion of the terminal ridge surface 92 between a dental appliance and the teeth to which the appliance is secured.

The inclined surface 90 of the pry lip 54 can act like a ramp-like portion or wedge to separate a dental appliance from the teeth when inserted therebetween. The dental appliance can move increasingly further away from the wearer's teeth by inserting a proximal base 127 of the inclined surface 90, which is adjacent the first perimeter 81, further toward the distal end of the teeth to which the dental appliance is mounted. The proximal base 127 has a thickness that is greater than the thickness $T_1$ of the terminal ridge surface 92. The inclined surface 90 can act like an inclined plane to allow the user to move the dental appliance away from the teeth with less force than otherwise would be used to do so.

The terminal ridge surface 92 is disposed a predetermined insertion distance $D_1$ along an insertion axis, in this case an axis parallel to the medial axis 100 and the planar sidewall 96 of the pry lip 54, from the proximal base 127 of the inclined surface 90 disposed at the perimeter 81 from which the pry lip extends to thereby define an insertion depth $D_1$ range of travel over which the terminal ridge surface 92 is insertable between a dental appliance and a wearer's teeth. The insertion depth $D_1$ and the bevel angle $\theta$ can be configured such that the terminal ridge surface 92 is limited from being inserted between the dental appliance and the wearer's tooth to such an amount that the apparatus 50 would gouge or injure the wearer's mouth.

Referring to FIG. 7, the second perimeter 85 is longer and wider than the first perimeter 81 of the body 52. The first perimeter 81 is disposed within the second perimeter 85 (see FIGS. 3 and 4 also). The curved portion 110 of the first end 56 of the body 52 has a radius $R_4$ of convex body end curvature along the transverse axis 66 of the curved portion 110 at the first end 56 of the body 52 that is approximately equal to an opposing radius $R_5$ of convex body end curvature along the transverse axis 66 of the curved portion 110 of the second end 57. The illustrated apparatus 50 of FIG. 7 has a radius $R_4$, $R_5$ of convex body end curvature of about 0.23 inches. In other embodiments, the radius $R_4$, $R_5$ of convex body end curvature can be different at each of the ends 56, 57. For example, in some embodiments, the radius $R_4$, $R_5$ of convex body end curvature can be about 0.18 inches. In still other embodiments, the radius $R_4$ of convex body end curvature at the first end 56 and the radius $R_5$ of convex body end curvature at the second end 57 can differ from each other.

The dental appliance removal device 50 can be made from any suitable material using known techniques. In some embodiments, the dental appliance removal device 50 is made from a suitable medical- and/or oral-grade plastic, such as an acetal resin commercially marketed by E. I. Du Pont de Nemours and Company of Wilmington, Del., as Delrin® acetal resin. The dental removal device 50 can be constructed using any suitable technique. In some embodiments, the dental appliance removal device 50 can be made using standard mold injection techniques.

Referring to FIGS. 8-15, another embodiment of an apparatus 150 for removing a dental appliance constructed in accordance with principles of the present disclosure is shown. In the embodiment of FIGS. 8-15, the dental appliance removal device 150 is somewhat horn-shaped in that it includes a bent portion 151 at one end. The removal device 150 is constructed such that it can be gripped by a user in a plurality of orientations.

Figure 8:
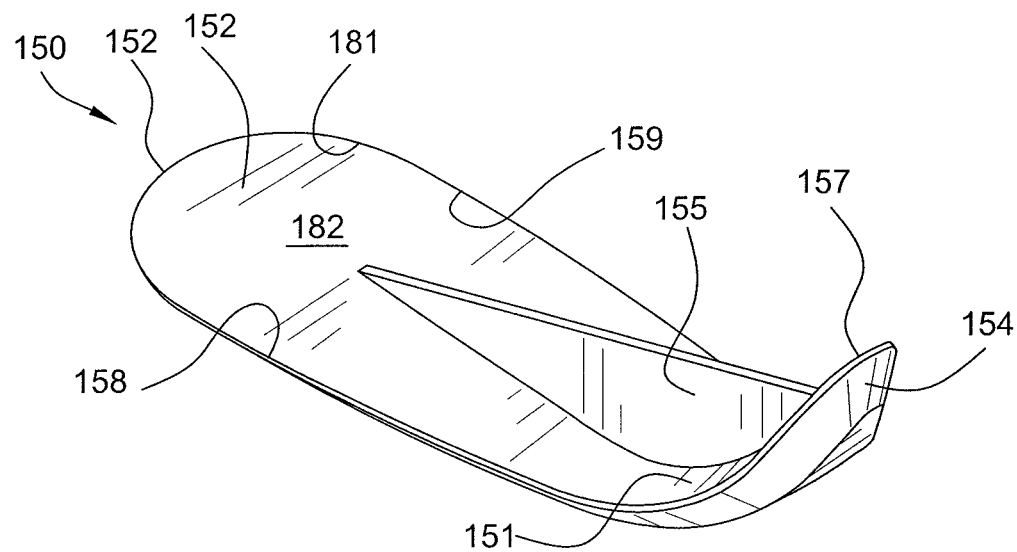
FIG. 8 is a perspective view of another embodiment of an apparatus for removing a dental appliance constructed according to principles of the present disclosure.
Figure 9:
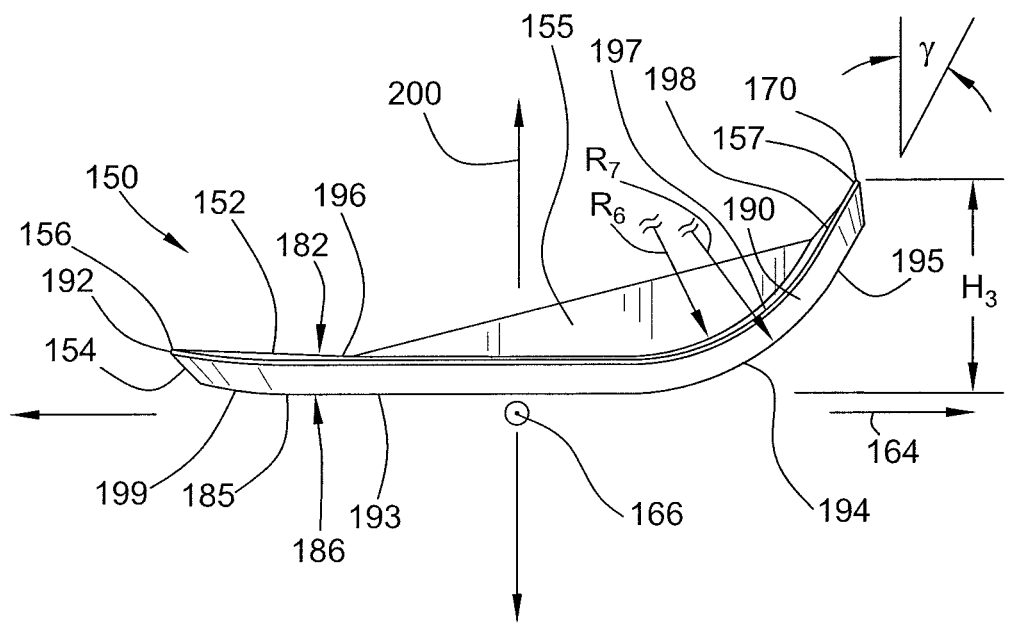
FIG. 9 is a side elevational view of the apparatus for removing a dental appliance of FIG. 8. The opposing side elevational view of the apparatus for removing a dental appliance of FIG. 8 is a mirror image of the view shown in FIG. 9.

Referring to FIGS. 8 and 9, the apparatus 150 for removing a dental appliance includes a body 152, a pry lip 154, and a gusset 155. The pry lip 154 circumscribes the body 152 and is adapted to facilitate the removal of a dental appliance from a wearer's teeth. The body 152 is configured to help allow a user to position a portion of the pry lip 154 in a plurality of orientations relative to a dental appliance mounted to the user's teeth.

The body 152 is generally elongate. The body 152 includes a pair of ends 156, 157 and a pair of sides 158, 159 in spaced relationship with each other that extend between the ends 156, 157. The ends 156, 157 and the sides 158, 159 are each mirror images of the other respective end and side. The body 152 is generally arcuate from the first end 156 to the second end 157.

The gusset or rib 155 extends from the body 152 along a central longitudinal axis 164 and spans the arcuate portion 151 of the body 152. The gusset 155 can help provide the body with structural rigidity and afford the user another gripping position.

Referring to FIGS. 8 and 9, the body 152 can include at least one perimeter that defines a face having a curved surface. The curved surface can be concave or convex. In the illustrated embodiment, the body 152 includes a first perimeter 181 defining a first face 182 with a concave surface and a second perimeter 185 defining a second face 186 with a convex surface.

The pry lip 154 can extend from one of the first and second perimeters 181, 185. In the illustrated embodiment of FIG. 9, the pry lip 154 extends from the second perimeter 185. The pry lip 154 includes an inclined surface 190 and a terminal ridge surface 192. The inclined surface 190 can be disposed between the terminal ridge surface 192 and the perimeter from which the pry lip 154 extends, in this case the second perimeter 185. The pry lip 154 can circumscribe the perimeter from which the pry lip 154 extends. The illustrated pry lip 154 of FIG. 15 circumscribes the second perimeter 185.

Referring to FIG. 10, the body 152 extends between the ends 156, 157 along the central longitudinal axis 164. The sides 158, 159 of the body 152 are in spaced relationship with each other along a transverse axis 166 that is perpendicular to the longitudinal axis 164. The first end 156 includes an end length apex 168 that is located substantially at a lateral midline 171 between the sides 158, 159 along the transverse axis 166. The second end 157 includes an end length apex 169 and an end height apex 170 that are both located substantially at the lateral midline 171. The first end length apex 168 and the second end height apex 170 of the body 152 are disposed on the first face 182, and the second end length apex 169 is disposed on the second face 186 (see FIGS. 11 and 14 also). Each side 158, 159 includes a body side apex 174, 175 that is located adjacent a curved portion 210 of the first end 156.

Referring to FIGS. 10 and 15, the first face 182 is in opposing relationship to the second face 186. The first perimeter 181 and the second perimeter 185 both generally taper between the first end 156 and the second end 157. Each side 158, 159 of the body 152 includes a tapered side portion 202 of the perimeters 181, 185. Each tapered side portion 202 of the first and second perimeters 181, 185 includes a pair of tapered segments 204, 205 that respectively taper toward each other from the first end 156 toward the second end 157 at a different amount. Each end 156, 157 of the body 152 includes a curved portion 210, 211 of the perimeters 181, 185.

Referring to FIG. 9, the second face 186 includes a planar base portion 193, a curved portion 194, and a planar inclined portion 195. The planar inclined portion 195 of the second face 186 is disposed at an oblique inclined angle γ with respect to a medial axis 200, which is perpendicular to the longitudinal axis 164 and the transverse axis 166. The inclined angle γ can be any suitable angle, such as an angle in a range between about 0° and about 80°, and more preferably in a range between about 10° and about 55°. The illustrated inclined angle γ is about 33°. The first face 182 is substantially the same as the second face 186 and includes a planar base portion 196, a curved portion 197, and a planar inclined portion 198. The second face can also include an undercut portion 199 adjacent the first end 156 which tapers slightly from the planar base portion 193 toward the first face 182.

Referring to FIG. 9, the concave surface of the first face 182 of the body 152 includes the curved portion 197 with a radius $R_6$ of concave body curvature. The curved portion 197 of the first face 182 of the body 152 is generally a cylindrical segment defined by a cylindrical axis that is substantially parallel to the transverse axis 166 disposed a radial distance $R_6$ from the curved portion 197. The gusset or rib 155 projects from the first face 182 and extends between at least two portions along the radius $R_6$ of concave body curvature.

The convex surface of the second face 186 of the body 152 includes the curved portion 194 with a radius $R_7$ of convex body curvature. The curved portion 194 of the second face 186 of the body 152 is generally a cylindrical segment defined by a cylindrical axis that is substantially parallel to the transverse axis 166 disposed a radial distance $R_7$ from the curved portion 194. The radius $R_7$ of convex body curvature can be greater than the radius $R_6$ of concave body curvature.

The illustrated apparatus 150 of FIG. 9 has a radius $R_6$ of concave body curvature of about 0.8 inches and a radius $R_7$ of convex body curvature of about 0.9 inches. In other embodiments, the radius $R_6$ of concave body curvature can be in a range from about a half inch to about 1½ inches. The radius $R_7$ of convex body curvature can be in a range from about half inch to about 1½ inches.

The ratio of the radius $R_7$ of convex body curvature to the radius $R_6$ of concave body curvature is about 1.1. The ratio of the radius $R_7$ of convex body curvature to the radius $R_6$ of concave body curvature can be in a range from greater than one to about 2, and in other embodiments, in a range from greater than one to about 1.5. In other embodiments, the radius $R_6$ of concave body curvature can be greater than the radius $R_7$ of convex body curvature.

The second end 157 is offset from the planar base portion 193 of the second face 186 of the body 152 along the medial axis 200 (see FIG. 14 also). The apparatus has a height $H_3$, measured along the medial axis 200 between the planar base portion 193 of the second face 186 of the body 152 and the first perimeter 181 of the body 152 at the second end height apex 170. In the illustrated embodiment, the height $H_3$ is about 0.6 inches. In other embodiments, the height of the apparatus for removing a dental appliance can be different. For example, in other embodiments, the height $H_4$ can be about 0.7 inches.

Referring to FIG. 10, the first perimeter 181 is longer and wider than the second perimeter 185 of the body 152. The second perimeter 185 is disposed within the first perimeter 181 (see FIGS. 11 and 15 also). The curved portion 210 of the first end 156 of the body 152 has a radius $R_8$ of convex body end curvature along the transverse axis 166. The illustrated apparatus 150 of FIG. 10 has a radius $R_8$ of convex body end curvature of about 0.3 inches. In other embodiments, the radius $R_8$ of convex body end curvature can be different. For example, in some embodiments, the radius $R_8$ of convex body end curvature can be about ⅜th of an inch.

Referring to FIG. 13, the second end 157 of the body 152 has a different shape than the first end 156 of the body 152. The second end 157 can define a segmented rounded hook.

Referring to FIG. 10, the pry lip 154 can be configured such that a user can grip the apparatus 150 at one of a plurality of different gripping locations and leave exposed at least one portion of the pry lip 154 for insertion between a dental appliance and the user's teeth to which the dental appliance is mounted. In conjunction with the curved shape of the body 152, the user can select one of a plurality of gripping positions to further facilitate the insertion of the pry lip 154 by providing a multitude of relative orientations between the pry lip 154 and the dental appliance mounted to the user's teeth.

Referring to FIGS. 13-15, the pry lip 154 includes a rounded tip portion 212, 213 extending around the curved portions 210 of the perimeters 181, 185 of the body 152. Each rounded tip portion 212, 213 of the pry lip 154 includes a pry lip end apex 214, 215 that is located substantially at the lateral midline 171 along the transverse axis 166. The pry lip 154 also includes a pair of sides 216, 217 having a pry lip side apex 220, 221 that is located near the curved portion 210 of the first end 156.

In some embodiments, the pry lip 154 can be configured such that a first pry lip portion is disposed adjacent to one of either the opposing ends 156, 157 or the opposing sides 158, 159 of the body 152 and a second pry lip portion is disposed adjacent to another one of the opposing ends 156, 157 and/or the opposing sides 158, 159 of the body 152. Accordingly, in some embodiments, the pry lip 154 can be configured such that a first pry lip portion is disposed adjacent to one of the opposing ends 156, 157 and a second pry lip portion is disposed adjacent to one of the opposing sides 158, 159 of the body 152. In yet other embodiments, the pry lip 154 can be configured such that the first and second pry lip portions are respectively disposed adjacent to the opposing ends 156, 157 of the body 152. In still other embodiments, the pry lip 154 can be configured such that the first and second pry lip portions are respectively disposed adjacent to the opposing sides 158, 159 of the body 152.

Referring to FIGS. 14 and 15, the illustrated pry lip 154 is configured such that it includes a pry lip portion 231, 232, 233, 234 respectively disposed adjacent to each of the opposing ends 156, 157 and the opposing sides 158, 159 of the body 152. The illustrated pry lip 154 extends continuously around the second perimeter 185 between the pry lip portions 231, 232, 233, 2134 such that the portions 231, 232, 233, 234 of the pry lip 154 are contiguous. In other embodiments, the pry lip portions 231, 232, 233, 234 can be discontinuous. In still other embodiments, the pry lip can include two or more pry lip portions disposed at different locations along the second perimeter 185.

Referring to FIG. 10, the apparatus 150 has a length $L_3$, measured along the central longitudinal axis 164 between the first end length apex 168 of the first perimeter 181 and the second end length apex 169 of the second perimeter 185 of the body 152, that is greater than the width $W_3$, measured along the transverse axis 166 between the body side apexes 174, 175 of the first perimeter 181. In the illustrated embodiment, the length $L_3$ is about 1.8 inches and the width $W_3$ is about 0.6 inches. In other embodiments, the length $L_3$ and the width $W_3$ can be different. For example, in some embodiments, the length $L_4$ can be about 2.2 inches and the width $W_4$ can be about 0.8 inches. In some embodiments, the apparatus can have a length-to-width ratio of about 2 or more. The illustrated embodiment of FIG. 8 has a length-to-width ratio of about 3. In yet other embodiments, the apparatus can have a length-to-width ratio of between about 2 and about 4.

In the illustrated embodiment, the length $L_3$ is greater than the height $H_3$. The illustrated embodiment of FIG. 8 has a length-to-height ratio of about 3.3. In other embodiments, the apparatus can have a different length, a different height, and/or a different length-to-height ratio. For example, in some embodiments, the apparatus can have a length-to-height ratio of about 2 or more. In still other embodiments, the apparatus can have a length-to-height ratio of between about 2 and about 4.

In still other embodiments, the apparatus can be scaled either upwardly or downwardly to be more convenient for a user to manipulate with either relatively large fingers and/or teeth or relatively small fingers and/or teeth. For example, in some embodiments the apparatus can have a length $L_4$ of about 2.2 inches, a width $W_4$ of about 0.8 inches, and a height $H_3$ of about 0.7 inches.

Referring to FIG. 12, the inclined surface 190 of the pry lip 154 is disposed adjacent the second perimeter 185 of the body 152. The terminal ridge surface 192 defines an oblique bevel angle α with respect to the inclined surface 190. The bevel angle α can be in a range between about 20° and about 75°. The illustrated bevel angle α is about 45°.

The terminal ridge surface 192 is adapted to be inserted between a dental appliance and the teeth to which the appliance is mounted. The terminal ridge surface 192 of the pry lip 154 can have a thickness $T_2$, measured between the first perimeter 181 and an outer perimeter 224 of the inclined surface 190, that is configured to facilitate the insertion of the pry lip 154 between a user's teeth and a dental appliance mounted thereto. In a preferred embodiment, the thickness $T_2$ of the terminal ridge surface 192 is about 0.025 inches or less, and even more preferably about 0.02 inches or less. The thickness $T_2$ of the illustrated terminal ridge surface 192 is about 0.015 inches.

The inclined surface 190 of the pry lip 154 can act like a ramp-like portion or wedge to separate a dental appliance from the teeth when inserted therebetween. The dental appliance can move increasingly further away from the wearer's teeth by inserting a proximal base 227 of the inclined surface 190, which is adjacent the second perimeter 185, further toward the distal end of the teeth to which the dental appliance is mounted. The proximal base 227 has a thickness that is greater than the thickness $T_2$ of the terminal ridge surface 192. The inclined surface 190 can act like an inclined plane to allow the user to move the dental appliance away from the teeth with less force than otherwise would be used to do so.

The terminal ridge surface 192 is disposed a predetermined insertion distance $D_2$, measured along an insertion axis 229 (in this case an axis generally perpendicular to the planar terminal ridge surface 192), from the second perimeter 185 of the body 152 and the proximal base 227 of the inclined surface 190 disposed at the second perimeter 185 from which the pry lip 154 extends to thereby define an insertion depth $D_2$ range of travel over which the terminal ridge surface 192 is insertable between a dental appliance and a wearer's teeth. The insertion depth $D_2$ and the bevel angle $\alpha$ can be configured such that the terminal ridge surface 192 is limited from being inserted between the dental appliance and the wearer's tooth to such an amount that the apparatus 50 would gouge or injure the wearer's gums.

The dental appliance removal device 150 can be made from any suitable material using known techniques. In some embodiments, the dental appliance removal device 50 is made from a suitable medical- and/or oral-grade plastic, such as an acetal resin commercially marketed by E. I. Du Pont de Nemours and Company of Wilmington, Del., as Delrin® acetal resin. The dental removal device 50 can be constructed using any suitable technique. In some embodiments, the dental appliance removal device 150 can be made using standard mold injection techniques.

Referring to FIGS. 16-22, another embodiment of a dental appliance removal device 250 constructed in accordance with principles of the present disclosure is shown. In the embodiment of FIGS. 16-22, the dental appliance removal device 250 is somewhat horn-shaped in that it includes a bent portion at one end. The removal device 250 is constructed such that it can be gripped by a user in a plurality of orientations.

Figure 16:
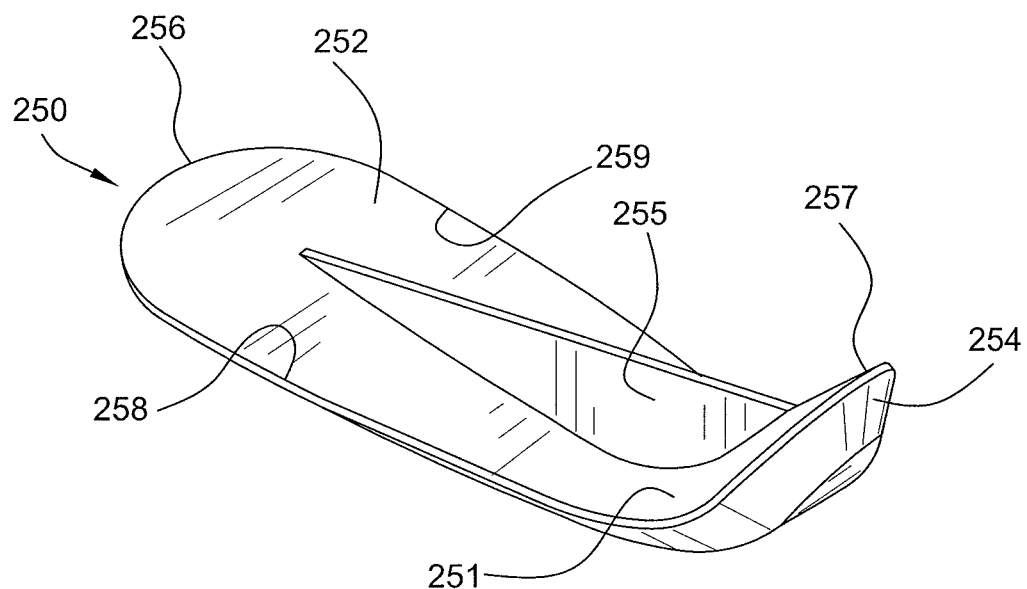
FIG. 16 is a perspective view of another embodiment of an apparatus for removing a dental appliance constructed according to principles of the present disclosure.
Figure 17:
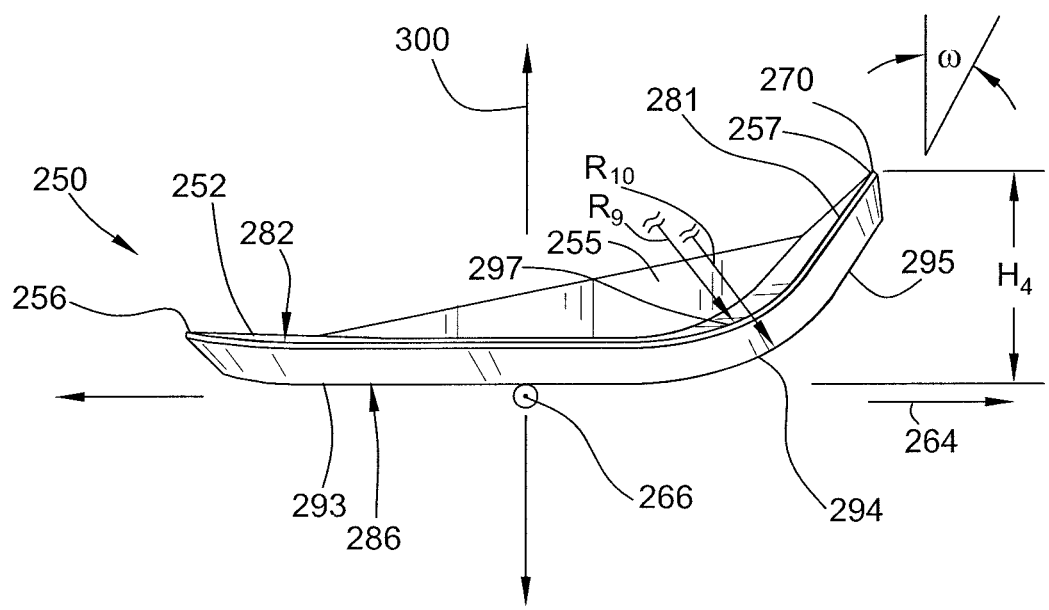
FIG. 17 is a side elevational view of the apparatus for removing a dental appliance of FIG. 16. The opposing side elevational view of the apparatus for removing a dental appliance of FIG. 16 is a mirror image of the view shown in FIG. 17.

Referring to FIGS. 16 and 17, the apparatus 250 for removing a dental appliance includes a body 252, a pry lip 254, and a gusset 255. The pry lip 254 circumscribes the body 252 and is adapted to facilitate the removal of a dental appliance from a wearer's teeth. The body 252 is configured to help allow a user to position a portion of the pry lip 254 in a plurality of orientations relative to a dental appliance mounted to the user's teeth to help the user position the pry lip in a way that removal of the dental appliance from the wearer's teeth can be achieved.

The body 252 is generally elongate. The body 252 includes a pair of ends 256, 257 and a pair of sides 258, 259 in spaced relationship with each other that extend between the ends 256, 257. The ends 256, 257 and the sides 258, 259 are each mirror images of the other respective end and side. The body 252 is generally arcuate from the first end 256 to the second end 257.

The gusset or rib 255 extends from the body 252 along the central longitudinal axis 264 and spans the arcuate portion 251 of the body 252. The gusset 255 can help provide the body with structural rigidity and afford the user another gripping position.

Referring to FIG. 17, a planar inclined portion 295 of the second face 286 is disposed at an oblique inclined angle $\omega$ with respect to a medial axis 300, which is perpendicular to the longitudinal axis 264 and the transverse axis 266. The inclined angle $\omega$ can be any suitable angle, such as an angle in a range between about 0° and about 80°, and more preferably in a range between about 10° and about 55°. The illustrated inclined angle $\omega$ is about 30°.

Referring to FIG. 17, the concave surface of the first face 282 of the body 252 includes a curved portion 297 with a radius $R_9$ of concave body curvature. The curved portion 297 of the first face 282 of the body 252 is generally a cylindrical segment defined by a cylindrical axis that is substantially parallel to the transverse axis 266 and disposed a radial distance $R_9$ from the curved portion 297. The gusset or rib 255 projects from the first face 282 and extends between at least two portions along the radius $R_9$ of concave body curvature.

The convex surface of the second face 286 of the body 252 includes a curved portion 294 with a radius $R_{10}$ of convex body curvature. The curved portion 294 of the second face 286 of the body 252 is generally a cylindrical segment defined by a cylindrical axis that is substantially parallel to the transverse axis 266 and disposed a radial distance $R_{10}$ from the curved portion 294. The radius $R_{10}$ of convex body curvature can be greater than the radius $R_9$ of concave body curvature.

The illustrated apparatus 250 of FIG. 18 has a radius $R_9$ of concave body curvature of about 0.7 inches and a radius $R_{10}$ of convex body curvature of about 0.8 inches. In other embodiments, the radius $R_9$ of concave body curvature and the radius $R_{10}$ of convex body curvature both can be different. For example, in some embodiments, the radius $R_9$ of concave body curvature and the radius $R_{10}$ of convex body curvature both can be in a range from about a half inch to about 1½ inches.

The ratio of the radius $R_{10}$ of convex body curvature to the radius $R_9$ of concave body curvature is about 1.2. The ratio of the radius $R_{10}$ of convex body curvature to the radius $R_9$ of concave body curvature can be different in other embodiments. For example, the ratio of the radius $R_{10}$ of convex body curvature to the radius $R_9$ of concave body curvature can be in a range from greater than one to about 2, and in other embodiments, in a range from greater than one to about 1.5. In other embodiments, the radius $R_9$ of concave body curvature can be greater than the radius $R_{10}$ of convex body curvature.

The second end 257 is offset from a planar base portion 293 of the second face 286 of the body 252 along the medial axis 300 (see FIG. 14 also). The apparatus has a height $H_4$, measured along the medial axis 300 between the planar base portion 293 of the second face 286 of the body 252 and the first perimeter 281 of the body 252 at a second end height apex 270 (found at a at a lateral midline 271 between the sides 258, 259 along the transverse axis 266 in this embodiment(see FIG. 18 also)). In the illustrated embodiment, the height $H_4$ is about 0.7 inches. In other embodiments, the height of the apparatus for removing a dental appliance can be different.

Figure 22:
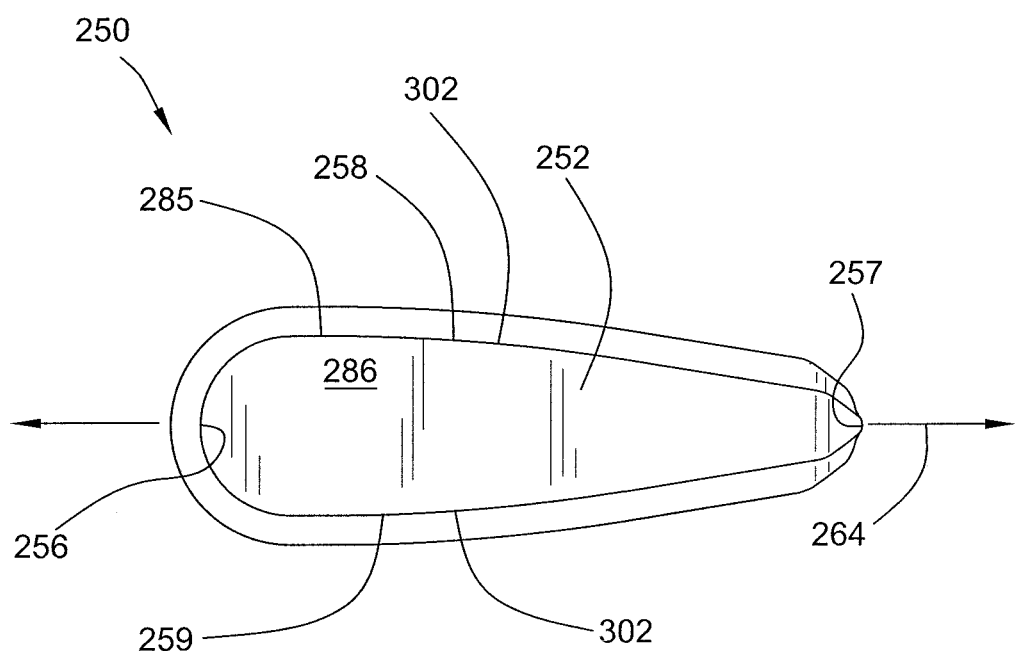
FIG. 22 is a bottom plan view of the apparatus for removing a dental appliance of FIG. 16.

Referring to FIGS. 18 and 22, a first face 282, defined by a first perimeter 281, of the body 252 is in opposing relationship to a second face 286, defined by a second perimeter 285, thereof. The first perimeter 281 and the second perimeter 285 both generally taper between the first end 256 and the second end 257 such that the second end 257 is narrower than the first end 256. The first perimeter 281 is longer and wider than the second perimeter 285 of the body 252. The second perimeter 285 is disposed within the first perimeter 281 (see FIGS. 20-22 also).

Referring to FIG. 18, a curved portion 310 of the first end 256 of the body 252 has a radius $R_{11}$ of convex body end curvature along the transverse axis 266. The illustrated apparatus 250 of FIG. 18 has a radius $R_{11}$ of convex body end curvature of about ⅜th of an inch. In other embodiments, the radius $R_{11}$ of convex body end curvature can be a different size.

Referring to FIG. 18, the apparatus 250 has a length $L_4$, measured along the central longitudinal axis 264 between a first end length apex 268 of the first perimeter 281 and a second end length apex 269 of the second perimeter 285 of the body 252 (see FIG. 19). Both the first and the second end length apexes 268, 269 are found at the lateral midline 271. The length $L_4$ of the apparatus 250 is greater than its width $W_4$, measured along the transverse axis 266 between a pair of body side apexes 274, 275 of the first perimeter 281 adjacent a rounded portion 310 of the first end 256. In the illustrated embodiment the length $L_4$ is about 2.2 inches and the width $W_4$ is about three-fourths of an inch. In other embodiments, the length $L_4$ and the width $W_4$ can be different. In some embodiments, the apparatus can have a length-to-width ratio of about 2 or more. The illustrated embodiment of FIG. 16 has a length-to-width ratio of about 3. In yet other embodiments, the apparatus can have a length-to-width ratio of between about 2 and about 4.

In the illustrated embodiment, the length $L_4$ is greater than the height $H_4$. The illustrated embodiment of FIG. 16 has a length-to-height ratio of about 3.3. In other embodiments, the apparatus can have a different length, a different height, and/or a different length-to-height ratio. For example, in some embodiments, the apparatus can have a length-to-height ratio of about 2 or more. In still other embodiments, the apparatus can have a length-to-height ratio of between about 2 and about 4.

Referring to FIGS. 18 and 22, each side 258, 259 of the body 252 includes a tapered side portion 302 of the perimeters 281, 285. The tapered side portions are mirror images of each other about the longitudinal axis 264. Each tapered side portion 302 is generally curved and tapers toward each other from the first end 256 toward the second end 257. The apparatus 250 for removing a dental appliance of FIG. 16-22 is similar in construction and functionality in other respects to the apparatus 150 for removing a dental appliance of FIG. 8-15.

Figure 23:
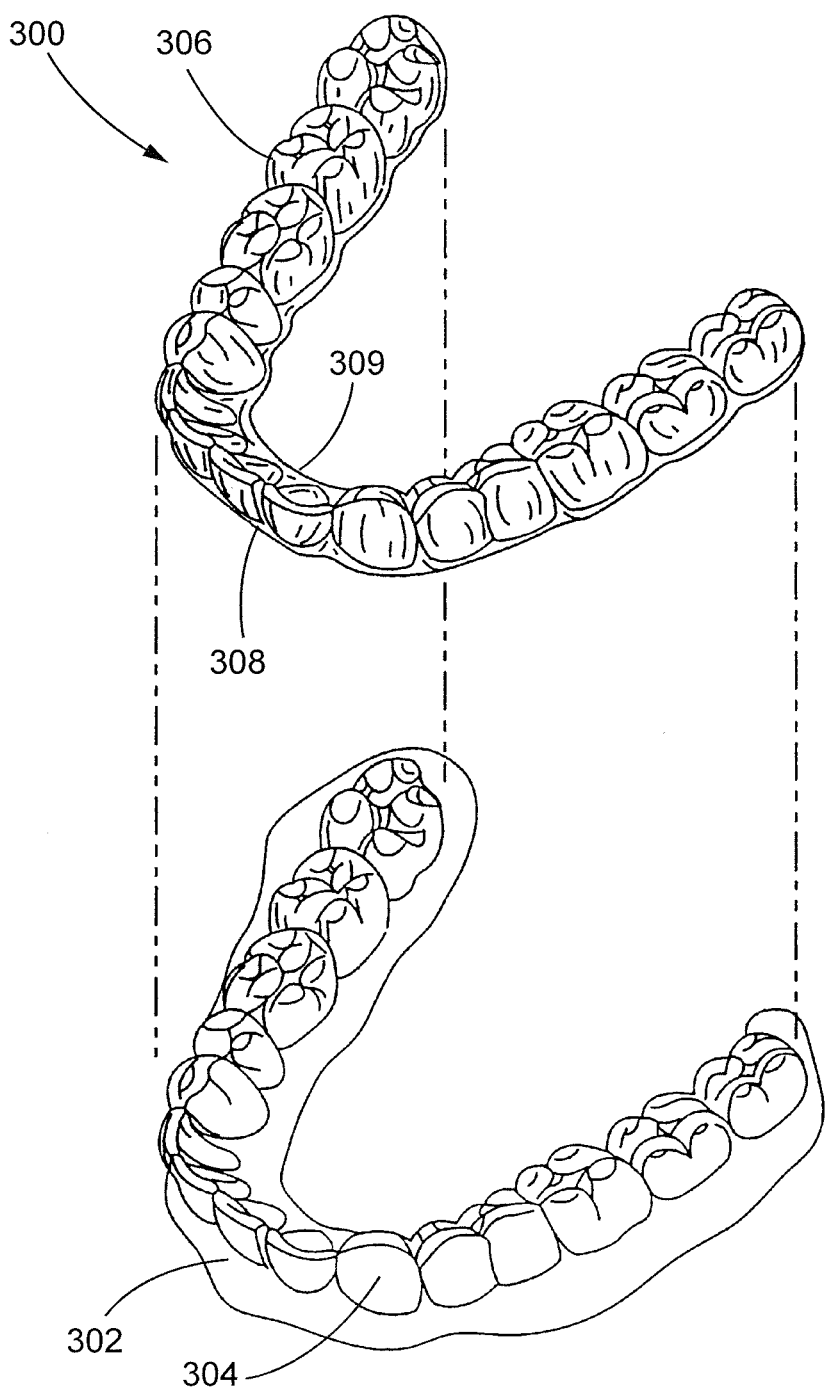
FIG. 23 is an exploded view of a user's lower jaw and an embodiment of a dental appliance suitable for use with an apparatus for removing a dental appliance and in a dental system constructed according to principles of the present disclosure.
Figure 24:
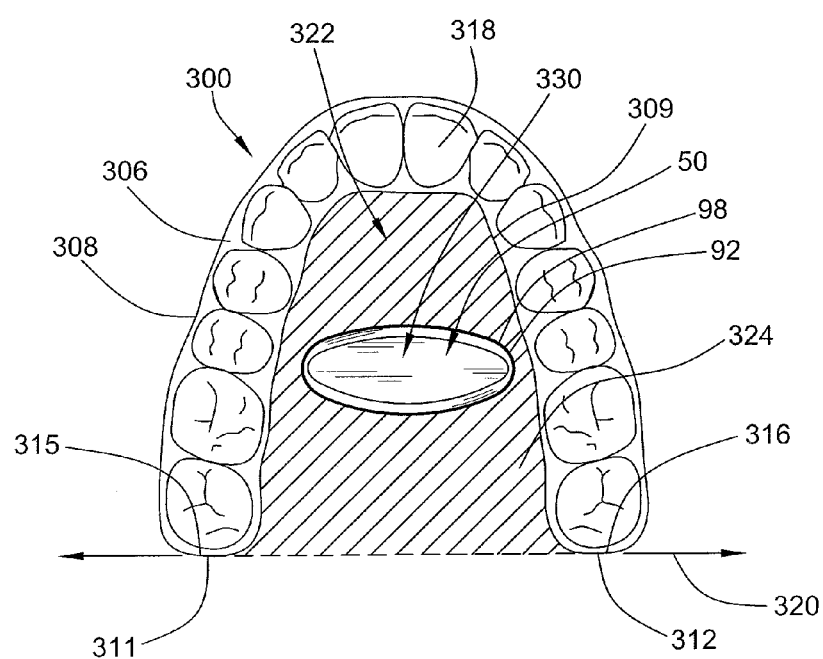
FIG. 24 is a top plan view of the dental appliance of FIG. 23 and a top plan view of the apparatus for removing a dental appliance of FIG. 1 disposed within an outer edge of the dental appliance.
Figure 25:
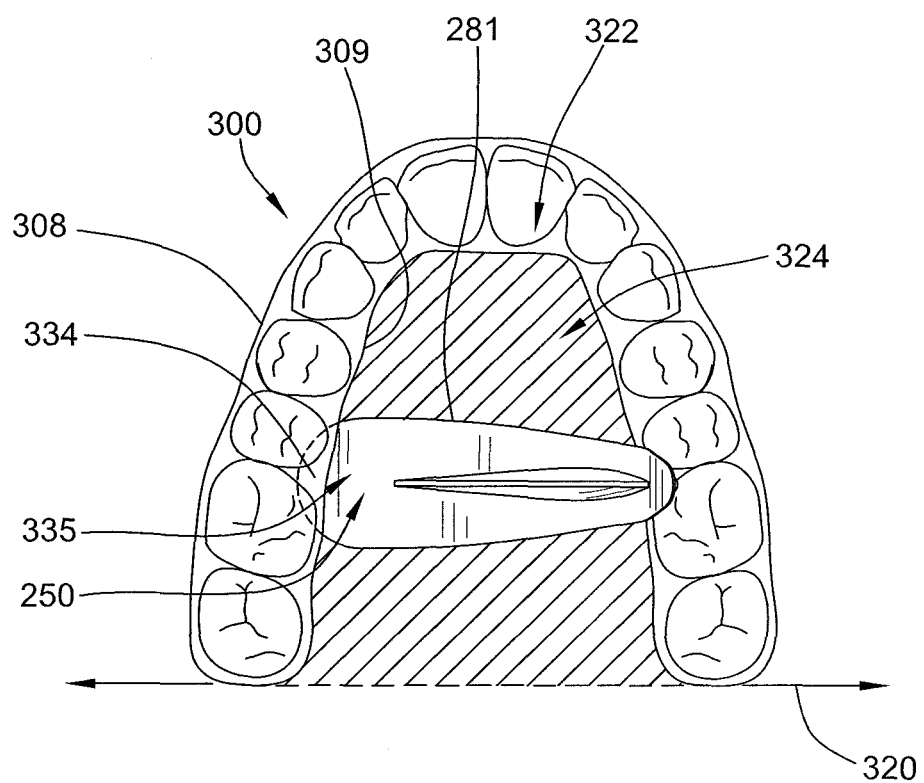
FIG. 25 is a top plan view of the dental appliance of FIG. 23 and the apparatus for removing a dental appliance of FIG. 8 disposed within an outer edge of the dental appliance.

Referring to FIGS. 23-25, an embodiment of a dental appliance 300 is shown. The dental appliance 300 is suitable for use with an apparatus for removing a dental appliance constructed according to principles of the present disclosure, such as those shown in FIGS. 1-22, for example.

Referring to FIG. 23, the dental appliance 300 is shown disposed above a user's lower jaw 302 with a plurality of lower teeth 304. The illustrative dental appliance 300 comprises an incremental position adjustment dental appliance. The dental appliance 300 is adapted to move at least one of the lower teeth 304 from an initial tooth arrangement to another tooth arrangement.

The dental appliance 300 comprises a clear polymeric shell 306 defining a cavity shaped to receive and resiliently reposition the lower teeth 304 from one tooth arrangement to a successive tooth arrangement. The polymeric shell 306 can, but need not, fit over all the lower teeth 304 present in the lower jaw 302. In some embodiments, the shell 306 is configured such that at least one of the lower teeth 304 will be repositioned when the dental appliance 300 is worn. In some embodiments, at least one of the teeth 304 not being repositioned can provide a base or anchor region for holding the dental appliance 300 in place as it applies the resilient repositioning force against the lower tooth or teeth 304 to be repositioned. In other embodiments, the shell 306 is configured to reposition most or all of the lower teeth 304. In such cases, the teeth 304 which are moved can also serve as a base or anchor region for holding the dental appliance 300. The shell 306 can also be configured such that the gums and/or the palette can serve as an anchor region, thereby allowing all or nearly all of the teeth 304 to be repositioned simultaneously. Additionally, anchors and adhesives can be provided which can also serve as attachment points for the dental appliance 300.

The shell 306 can be forced down over the lower teeth 304, typically by the user biting down on the shell or by applying manual pressure to the shell 306 with the user's fingers. An outer edge 308 and an inner edge 309 can be made such that they are adapted to engage the undercut U shape of the teeth 304 to hold the shell 306 in place on the teeth 304.

The shell 306 can be made of a material that has a predetermined modulus, also referred to as the stiffness, of the material. The modulus can be predetermined to produce the desired repositioning of the teeth based on requirements set by an individual user's repositioning needs. In one example, the shell 306 can have a modulus in a range between about 0.1 GPa to about 4 GPa. The stiffness, or modulus, of the shell 306 keeps the edges 308, 309 engaged with the lower teeth 304 such that the dental appliance 300 is held in place on the lower jaw 302 and effects tooth repositioning. Various known techniques can be used to vary the stiffness of the shell 306 to facilitate the removal of the dental appliance 300 from the lower jaw 302.

A user may have a second dental appliance adapted for use with the user's upper jaw. Also, a plurality of such dental appliance can be included in a dental system wherein the dental appliances are configured to be worn by a user successively in order to achieve the gradual tooth repositioning. The dental appliances can comprise a plurality of incremental position adjustment appliances. One or more additional incremental position adjustment dental appliances can be provided which each have a geometry selected to progressively reposition a user's teeth from an existing arrangement to a successive arrangement.

A different dental appliance can be used in other embodiments. Examples of a dental appliance suitable for use with a dental appliance removal device constructed according to principles of the present disclosure includes those shown and described in U.S. Pat. Nos. 5,975,893 and 6,183,248 and those commercially available from, and marketed as invisalign® aligners by, Align Technology, Inc. of San Jose, Calif. Such a dental appliance can be made using known construction techniques.

Referring to FIG. 24, the dental appliance 300 includes a pair of end edges 311, 312 that extend between the U-shaped outer edge 308 and inner edge 309. The edges 308, 309, 311, 312 of the dental appliance 300 define a pair of ends 315, 316 and a generally arcuate segment 318 extending between the ends 315, 316. The arcuate segment 318 is generally U-shaped and follows the shape of the outer edge 308 and the inner edge 309. The outer edge 308 is convex and the inner edge 309 is concave. The outer edge 308, the inner edge 309 and the end edges 311, 312 define an opening to the cavity of the shell 306.

The end edges 311, 312 define an end axis 320. The outer edge 308 and the end axis 315 define an inscribed dental appliance area 322 with a first shape. The dental appliance area 322 includes the area between the inner edge 309, the outer edge 308, and the end edges 311, 312.

The inner edge 308 and the end axis 320 define a recess 324, shown with cross-hatching in FIG. 24. The dental appliance area 322 includes the recess 324 and the area bounded by the inner edge 309, the outer edge 308, and the end edges 311, 312.

A dental appliance removal device constructed according to principles of the present disclosure can be configured such that it can fit within the dental appliance area 322 of the dental appliance 300. For example, the apparatus 50 for removing a dental appliance of FIGS. 1-7 is shown disposed within the recess 324 of the dental appliance 300.

The outer perimeter 98 of the terminal ridge surface 92 of the apparatus 50 for removing a dental appliance comprises an outer edge that defines a remover area 330 with a second shape. The apparatus 50 for removing a dental appliance is configured such that the remover area 330 is not greater than the dental appliance area 322 and the second shape of the remover area 330 can be disposed within the first shape of the dental appliance area 322.

Referring to FIG. 25, the apparatus 250 for removing a dental appliance of FIGS. 16-22 is shown disposed within the dental appliance area 322 of the dental appliance 300. The first perimeter 281 of the body 252 of the apparatus 250 for removing a dental appliance comprises an outer edge that defines a remover area 335 with a second shape. The apparatus 250 for removing a dental appliance is configured such that the remover area 335 is not greater than the dental appliance area 322 and the second shape of the remover area 335 can be disposed within the first shape of the dental appliance area 322. In this arrangement, a portion 334 of the dental appliance removal device 250 extends beyond the recess 324 of the dental appliance 300 and is disposed between the inner edge 309 and the outer edge 308 of the dental appliance 300. The remover area 335 is less than the dental appliance area 322. The second shape of the remover area 335 of the apparatus 250 does not extend beyond the outer edge 308 of the dental appliance 300.

Figure 26:
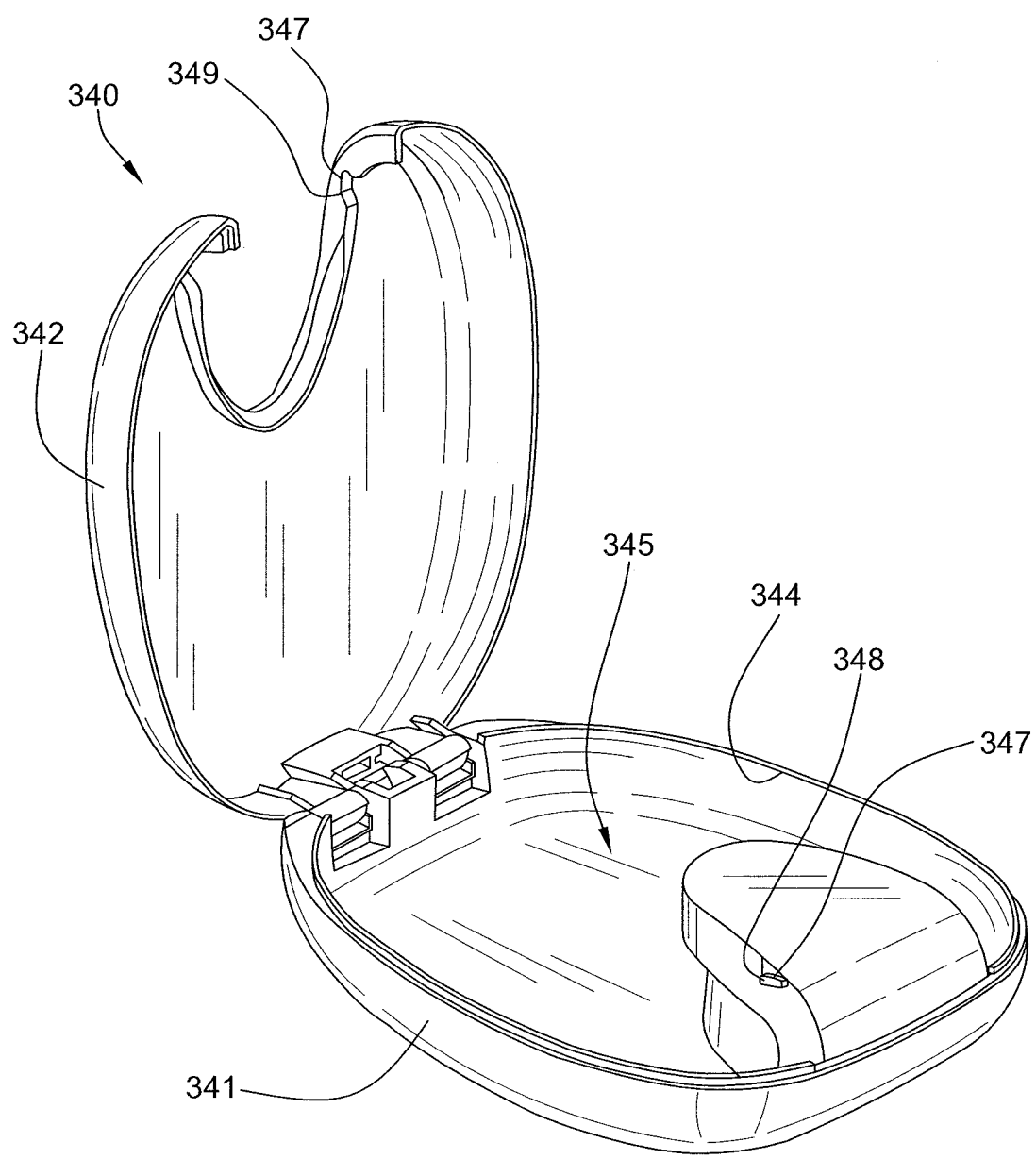
FIG. 26 is a perspective view of an embodiment of a dental appliance container suitable for use in a dental system constructed according to principles of the present disclosure.

Referring to FIG. 26, an embodiment of a dental appliance container 340 is shown. The dental appliance holder 340 includes a base 341 and a lid 342. The base 341 defines an opening 344 and an interior cavity 345 in communication with the opening 344. The interior cavity 345 is adapted to accommodate at least one dental appliance and an apparatus for removing a dental appliance constructed according to principles of the present disclosure.

The lid 342 can be adapted to be positioned in relation to the base 341 so that the lid 342 at least partially occludes the opening 344 of the base 341 when the lid 342 is in a closed position. In this embodiment, the lid 342 is pivotally mounted to the base 341 such that the lid is movable over a range of travel between the closed position and a range of open positions. A closure mechanism 347 can be provided to selectively retain the lid 342 in the closed position. The closure mechanism 347 can include at least one retaining finger 348 adapted to retaining engage a notch 349 in the lid 347. In the illustrated embodiment, the closure mechanism includes a pair of retaining fingers 348 arranged to respectively engage a pair of notches 349.

The dental appliance container 340 can be made from any suitable material, such as a suitable plastic, for example, using known construction techniques. In other embodiments, the dental appliance container can take other forms.

Figure 27:
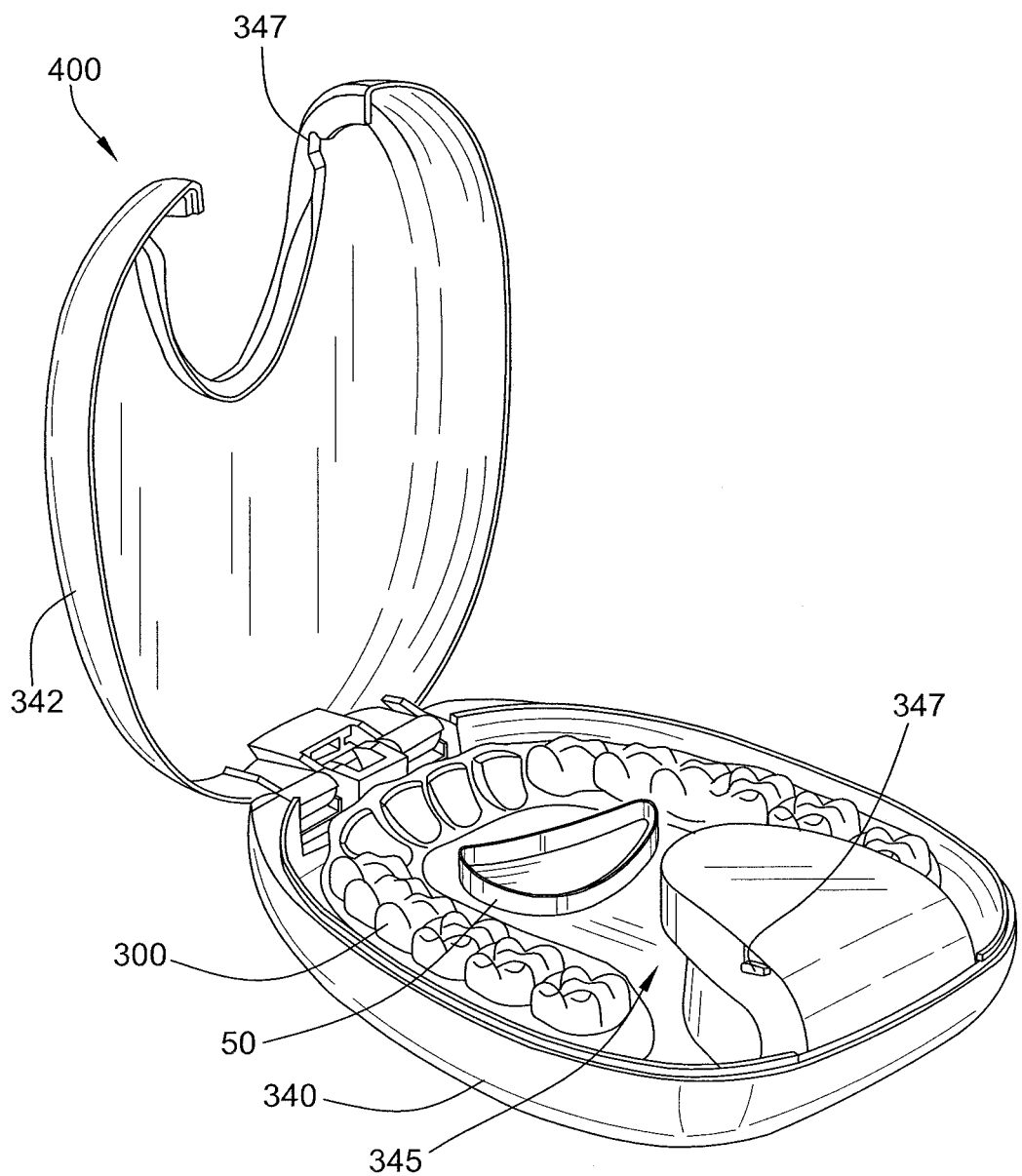
FIG. 27 is a perspective view of an embodiment of a dental system constructed according to principles of the present disclosure.

Referring to FIG. 27, an embodiment of a dental system 400 is shown. The dental system 400 includes the apparatus 50 for removing a dental appliance of FIG. 1, the dental appliance 300 of FIG. 23, and the dental appliance container 340 of FIG. 26. The dental system 400 is configured such that both the apparatus 50 for removing a dental appliance and the dental appliance 300 can be stored within the interior cavity 345 of the container 340. The lid 342 is operable to move over a range of travel between a plurality of open positions and the closed position. The lid 342 can be moved to the closed position and secured with the closure mechanism 347 to store both the apparatus 50 for removing a dental appliance and the dental appliance 300 within the interior cavity 345 of the container 340.

Figure 28:
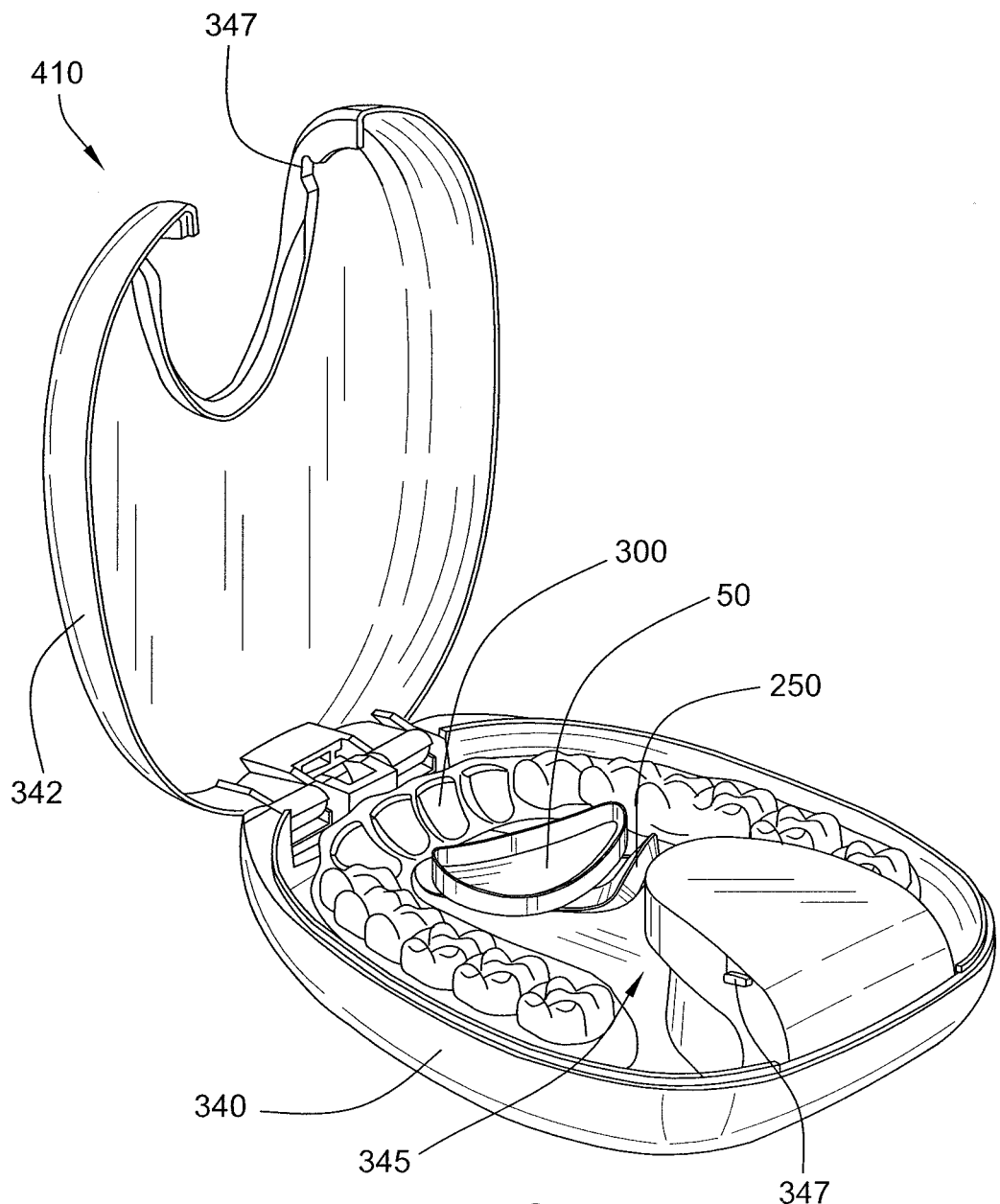
FIG. 28 is a perspective view of another embodiment of a dental system constructed according to principles of the present disclosure.

Referring to FIG. 28, another embodiment of a dental system 410 is shown. The dental system 410 includes the apparatus 50 for removing a dental appliance of FIG. 1, the apparatus 250 for removing a dental appliance of FIG. 16, the dental appliance 300 of FIG. 23, and the dental appliance container 340 of FIG. 26. The dental system 410 is configured such that both dental appliance removal devices 50, 250 and the dental appliance 300 can be stored within the interior cavity 345 of the container 340. The lid 342 is operable to move over a range of travel between a plurality of open positions and the closed position. The lid 342 can be moved to the closed position and secured with the closure mechanism 347 to store both dental appliance removal devices 50, 250 and the dental appliance 300 within the container 340.

Figure 29:
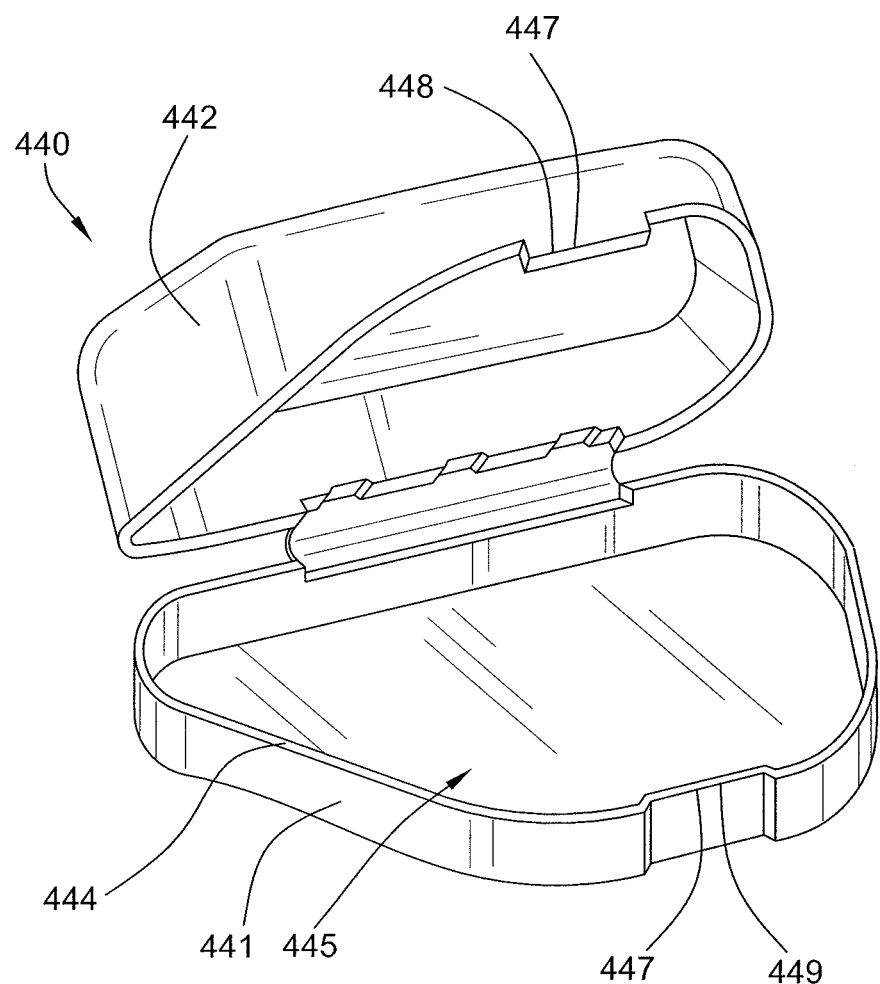
FIG. 29 is a perspective view of another embodiment of a dental appliance container suitable for use in a dental system constructed according to principles of the present disclosure.

Referring to FIG. 29, another embodiment of a dental appliance container 440 is shown. The dental appliance holder 440 includes a base 441 and a lid 442. The base 441 defines an opening 444 and an interior cavity 445 in communication with the opening 444. The interior cavity 445 is adapted to accommodate at least one dental appliance and an apparatus for removing a dental appliance constructed according to principles of the present disclosure.

The lid 442 can be adapted to be positioned in relation to the base 441 so that the lid 442 at least partially occludes the opening 444 of the base 441 when the lid 442 is in a closed position. In this embodiment, the lid 442 is pivotally mounted to the base 441 such that the lid 442 is movable over a range of travel between the closed position and a range of open positions. A closure mechanism 447 can be provided to selectively retain the lid 442 in the closed position. The closure mechanism 447 can include at least one retaining finger 448 adapted to retaining engage a notch 449 in the lid 447. In the illustrated embodiment, the closure mechanism includes a single retaining finger 448 arranged with a single notch 449. The dental appliance 440 of FIG. 29 is smaller than the dental appliance container 340 of FIG. 26.

Figure 30:
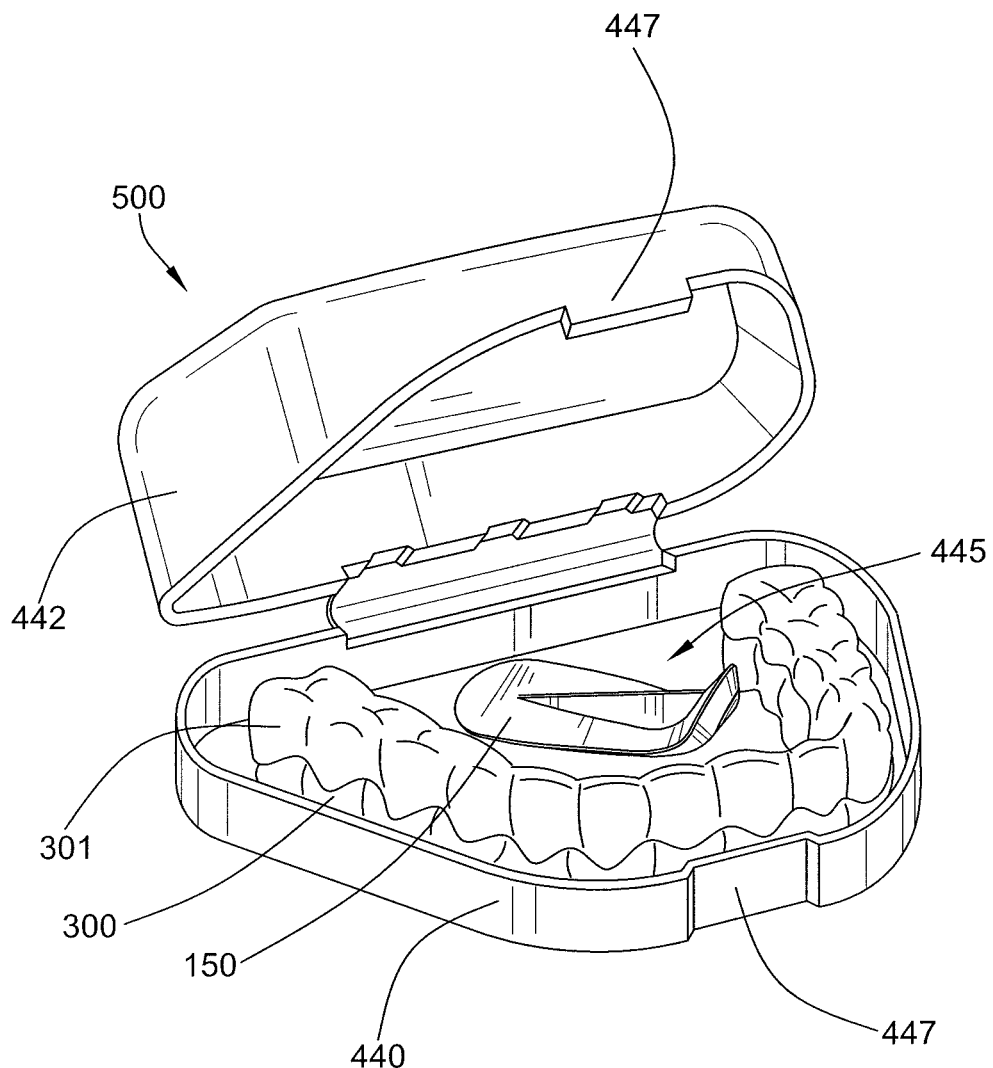
FIG. 30 is a perspective view of still another embodiment of a dental system constructed according to principles of the present disclosure.

Referring to FIG. 30, another embodiment of a dental system 500 is shown. The dental system 500 includes the apparatus 150 for removing a dental appliance of FIG. 8, the dental appliance 300 of FIG. 23, a dental appliance 301 similar to the dental appliance 300 of FIG. 23 except that it is configured for the teeth of the user's upper jaw, and the dental appliance container 440 of FIG. 29. The dental system 500 is configured such that the apparatus 150 for removing a dental appliance and the dental appliances 300, 301 can be stored within the interior cavity 445 of the container 440. The lid 442 is operable to move over a range of travel between a plurality of open positions and the closed position. The lid 442 can be moved to the closed position and secured with the closure mechanism 447 to store the apparatus 150 for removing a dental appliance and both of the dental appliances 300, 301 within the container 440.

Figure 31:
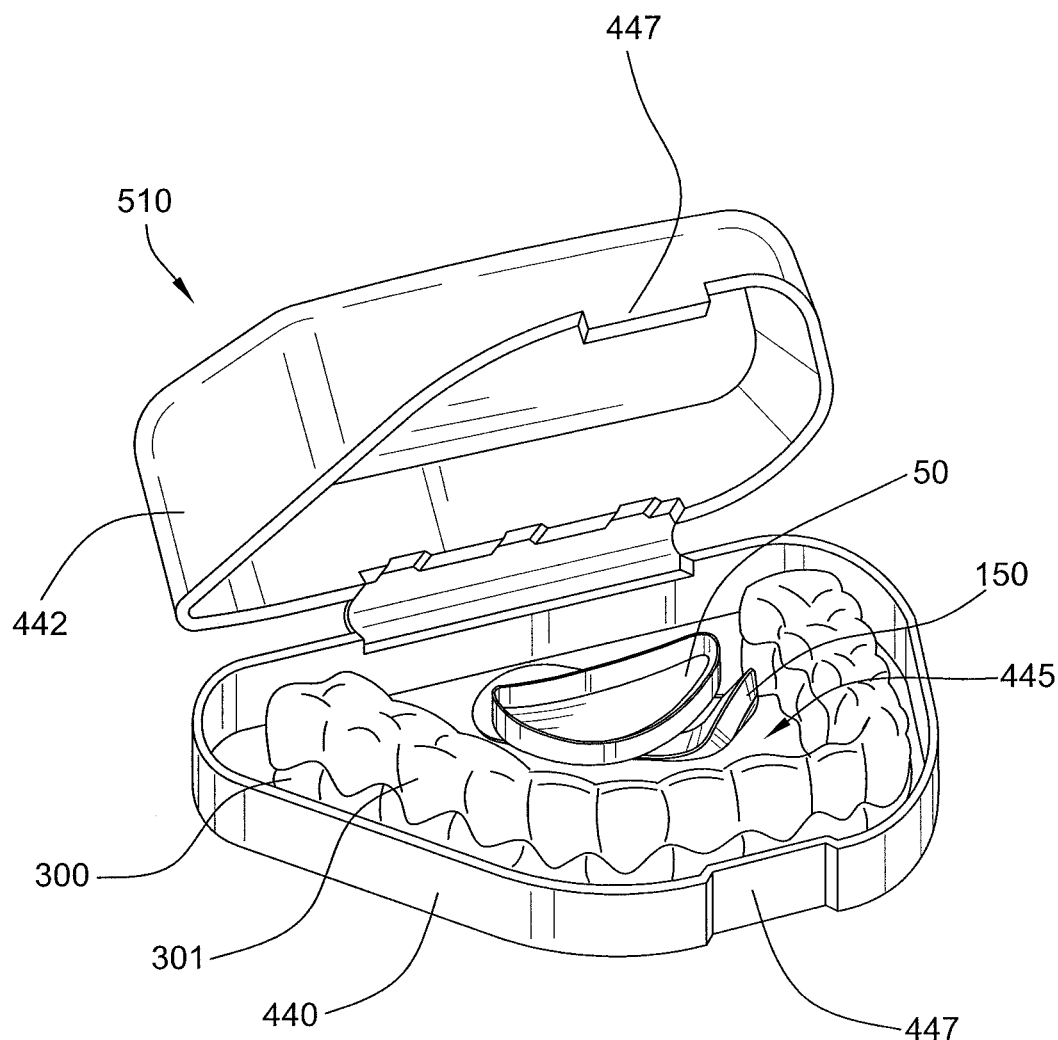
FIG. 31 is a perspective view of yet another embodiment of a dental system constructed according to principles of the present disclosure.

Referring to FIG. 31, another embodiment of a dental system 510 is shown. The dental system 510 includes the apparatus 50 for removing a dental appliance of FIG. 1, the apparatus 150 for removing a dental appliance of FIG. 8, the dental appliance 300 of FIG. 23, a dental appliance 301 similar to the dental appliance 300 of FIG. 23 except that it is configured for the teeth of the user's upper jaw, and the dental appliance container 440 of FIG. 29. The dental system 510 is configured such that both of the dental appliance removal devices 50, 150 and both of the dental appliances 300, 301 can be stored within the interior cavity 445 of the container 440. The lid 442 is operable to move over a range of travel between a plurality of open positions and the closed position. The lid 442 can be moved to the closed position and secured with the closure mechanism 447 to store the dental appliance removal devices 50, 150 and the dental appliances 300, 301 within the container 440.

In other embodiments, the components of a dental system constructed according to principles of the present disclosure can be varied. For example, in other embodiments, the dental appliance can be a different type, such as a retainer. In yet other embodiments, the number of dental appliances and/or dental appliance removal devices can be varied. In still other embodiments, a plurality of dental appliance removal devices can be provided that are substantially the same except that at least one has a different proportional shape than the remainder.

A dental appliance removal device constructed according to principles of the present disclosure can be used to remove a dental appliance, such as the dental appliance 300 of FIG. 23, from a wearer's teeth. A terminal ridge surface of the dental appliance removal device can be inserted along an insertion axis between one of the inner and outer edges of the dental appliance and the wearer's teeth. As the terminal ridge surface is moved toward the distal end of the wearer's teeth, an inclined surface of the dental appliance removal device acts as an inclined plane to facilitate the separation of the selected edge of the dental appliance in a direction generally perpendicular to the insertion axis. The wearer can grip the separated edge and effect removal of the dental appliance from the wearer's teeth. The inclined surface can be configured to provide an insertion depth limit so that the terminal ridge surface is not readily inserted between the wearer's teeth and the dental appliance beyond a predetermined limit.

Advantageously, in some embodiments, at least one dental appliance removal device can be provided in a dental system that includes one or more dental appliances and a dental appliance container adapted to store the dental appliance(s) and the dental appliance removal device(s) in the container. The dental appliance removal device(s) can be stored with the dental appliance(s) in the dental appliance container to thereby be readily available when a dental appliance wearer removes a dental appliance, which is typically stored in the dental appliance container when not being worn. The dental appliance removal device(s) can be configured so that they are compact and sized to be stored within an outer footprint defines by the dental appliance(s).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A dental system comprising:
    a dental appliance including an outer edge defining a dental appliance area with it first shape;
    an apparatus for removing a dental appliance including an outer edge defining a remover area with a second shape, the apparatus including:
        a body, the body including a perimeter, the perimeter of the body defining a face having a curved surface,
        a pry lip, the pry lip extending from and circumscribing the entire perimeter of the body, the pry lip including an inclined surface and a terminal ridge surface, the inclined surface disposed between the terminal ridge surface and the perimeter of the body;
    wherein the apparatus for removing a dental appliance is configured such that the second shape of the remover area is disposable within the first shape of the dental appliance area.

2. The dental system according to claim 1, wherein the dental appliance comprises an incremental position adjustment dental appliance.

3. The dental system according to claim 2, further comprising:
    one or more additional incremental position adjustment dental appliances each having a geometry selected to progressively reposition a user's teeth from an arrangement to a successive arrangement.

4. The dental system according to claim 2, wherein the incremental position adjustment dental appliance has a pair of ends and a generally arcuate segment extending between the ends, the arcuate segment including the outer edge of the dental appliance and an inner edge, the outer edge being convex and the inner edge being concave, the inner edge and the ends defining a recess, and the dental appliance area including the recess.

5. The dental system according to claim 1, wherein the dental appliance has a pair of ends and a. generally arcuate segment extending between the ends, the arcuate segment including the outer edge of the dental appliance and an inner edge, the outer edge being convex and the inner edge being concave, the inner edge and the ends defining a recess, and the dental appliance area including the recess.

6. The dental system according to claim 1, further comprising:
   a dental appliance holder including a base and a lid, base defining an opening and an interior cavity in communication with the opening, the interior cavity adapted to accommodate both the dental appliance and the apparatus for removing a dental appliance, the lid adapted to be positioned in relation to the base so that the lid at least partially occludes the opening of the base.

* * * * *